United States Patent
Gao et al.

(10) Patent No.: US 10,948,467 B2
(45) Date of Patent: Mar. 16, 2021

(54) ONLINE CENTRALIZED MONITORING AND ANALYSIS METHOD FOR MULTI-POINT MALODOROUS GASES USING ELECTRONIC NOSE INSTRUMENT

(71) Applicant: EAST CHINA UNIVERSITY OF SCIENCE AND TECHNOLOGY, Shanghai (CN)

(72) Inventors: Daqi Gao, Shanghai (CN); Xiaoqin Zhang, Shanghai (CN); Zejian Wang, Shanghai (CN); Liming Zhao, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 16/642,531

(22) PCT Filed: May 30, 2018

(86) PCT No.: PCT/CN2018/088913
§ 371 (c)(1),
(2) Date: Feb. 27, 2020

(87) PCT Pub. No.: WO2019/218395
PCT Pub. Date: Nov. 21, 2019

(65) Prior Publication Data
US 2020/0400631 A1    Dec. 24, 2020

(30) Foreign Application Priority Data

May 17, 2018 (CN) .......................... 201810471613.1
May 17, 2018 (CN) .......................... 201810471708.3

(51) Int. Cl.
*G01N 33/00* (2006.01)
*G01N 27/64* (2006.01)
(Continued)

(52) U.S. Cl.
CPC ........... *G01N 33/0006* (2013.01); *G01N 1/24* (2013.01); *G01N 27/12* (2013.01); *G01N 27/403* (2013.01);
(Continued)

(58) Field of Classification Search
CPC ...... G01N 33/0006; G01N 1/24; G01N 27/12; G01N 27/403; G01N 27/64;
(Continued)

(56) References Cited

U.S. PATENT DOCUMENTS 5,756,879 A * 5/1998 Yamagishi ........... G01N 27/126
                                                              204/424
5,766,551 A * 6/1998 DiSpirito ............. G01N 1/2226
                                                              422/63
(Continued)

FOREIGN PATENT DOCUMENTS

CN        1367381 A1 *  9/2002
CN        1482453 A1 *  3/2004
(Continued)

OTHER PUBLICATIONS

Machine Translation of CN-1367381-A Which Originally Published on Sep. 4, 2002 and Corresponds to Chinese Patent Application CN 02111046.8. (Year: 2002).*

(Continued)

*Primary Examiner* — David A. Rogers
(74) *Attorney, Agent, or Firm* — Workman Nydegger

(57) ABSTRACT

Provided is an online centralized monitoring and analysis system using an electronic nose instrument for multi-point malodorous gases, and the system includes an electronic nose instrument, which connects with multiple monitoring points through pipes. On-site malodorous gases in the maximum range of 2.5 km are drawn into the electronic nose instrument within 1 min by the external vacuum pump, and
(Continued)

forced to flow through an annular working chamber of a gas sensor array for 30 s by the internal vacuum pump periodically. The modular convolution neural networks online learn the recent time-series responses of the gas sensor array and predict their coming responses, and the modular deep neural networks offline set up the relationship between the responses and multiple concentration items according to odor big data. The electronic nose instrument monitors up to 10 pollution sites cyclically and uses the cascade machine learning model to online predict one dimensionless odor-unit (OU) concentration index value and 10 specified-component concentration index values of malodorous gases.

11 Claims, 9 Drawing Sheets

(51) Int. Cl.
| | | |
|---|---|---|
| *G06N 3/08* | (2006.01) | |
| *G01N 1/24* | (2006.01) | |
| *G01N 27/403* | (2006.01) | |
| *G06N 3/04* | (2006.01) | |
| *G01N 27/12* | (2006.01) | |

(52) U.S. Cl.
CPC ......... *G01N 27/64* (2013.01); *G01N 33/0016* (2013.01); *G01N 33/0032* (2013.01); *G06N 3/0454* (2013.01); *G06N 3/084* (2013.01)

(58) Field of Classification Search
CPC ........... G01N 33/0016; G01N 33/0032; G06N 3/0454; G06N 3/084
See application file for complete search history.

(56) References Cited

U.S. PATENT DOCUMENTS

| | | | | |
|---|---|---|---|---|
| 6,033,630 | A * | 3/2000 | Hinton | G01N 27/126 338/13 |
| 6,672,129 | B1 * | 1/2004 | Frederickson | A61M 15/02 347/20 |
| 7,905,154 | B2 * | 3/2011 | Jones, Jr. | G01N 1/06 73/864.81 |
| 7,971,470 | B2 * | 7/2011 | Broz | G01N 33/46 73/31.03 |
| 8,038,948 | B1 * | 10/2011 | Laughlin | G01N 33/0073 422/83 |
| 8,272,280 | B2 * | 9/2012 | Jones, Jr. | G01N 33/12 73/864.81 |
| 8,312,759 | B2 * | 11/2012 | McAlister | G01N 35/00871 73/31.07 |
| 8,336,402 | B2 * | 12/2012 | Glezer | G01N 1/2273 73/863.81 |
| 8,394,330 | B1 * | 3/2013 | Lewis | G01N 27/126 422/98 |
| 9,442,889 | B2 * | 9/2016 | Chee | B60H 3/0035 |
| 10,078,044 | B2 * | 9/2018 | Akhondi | B01D 65/10 |
| 2008/0236249 | A1 * | 10/2008 | Fernandez de la Mora | G06K 9/00543 73/23.35 |
| 2013/0298642 | A1 * | 11/2013 | Gillette, II | G01M 15/102 73/31.01 |
| 2014/0332994 | A1 | 11/2014 | Danes et al. | |

FOREIGN PATENT DOCUMENTS

| | | |
|---|---|---|
| CN | 1173171 C | 10/2004 |
| CN | 1228625 | 11/2005 |
| CN | 101806763 A1 * | 8/2010 |
| CN | 102353798 | 2/2012 |
| CN | 101806763 | 11/2012 |
| CN | 103454335 | 12/2013 |
| CN | 103472094 | 12/2013 |
| CN | 103196830 | 3/2016 |
| CN | 105486812 | 4/2016 |
| CN | 107807199 | 3/2018 |
| CN | 107843695 | 3/2018 |

OTHER PUBLICATIONS

Machine Translation of CN-1482453-A Which Originally Published on Mar. 17, 2004 and Corresponds to Chinese Patent Application CN 03141537.7. (Year: 2004).*

Machine Translation of CN-101806763-A Which Originally Published on Aug. 18, 2010 and Corresponds to Chinese Patent Application CN 201010115026.2. (Year: 2010).*

Machine Translation of CN-103454335-A Which Originally Published on Dec. 18, 2013 and Corresponds to Chinese Patent Application CN 201310405315.X (Year: 2013).*

International Search Report issued in PCT/CN2018/088913 dated Feb. 20, 2019.

People's Daily Online "The Ministry of environmental Protection (MEP) said it received more than 600,000 environmental reports in 2017, accounting for nearly 60% of the total", 2018, htt://politics.people.com.cn/n1/2018/0123/c 1001-29782203. htr.

Alodorous pollution only depends on nose, Experts suggest that 24-hour monitoring should be implemented as soon as possible, Jul. 6, 2016.

Journal of Safety and Environment, vol. 15, No. 3, Jun. 2015, Research advances and prospects on the ol-factory thereshold of odor substance and its formation mechanism.

Xiang Wen-ying, et al., "Improvement of fuzzy comprehensive evaluation method and its application to the evaluation of reservoir water quality", Journal of Safety and Environment, vol. 15, No. 6, Dec. 2015.

Wang Gen, "Establishment and Application of Fingerprint of Malodorous Pollution Source", 2017.

Wang Jinnan, et al., "Strategic Ideas on the 13th Five-Year Plan of National environmental Protection", China Academic Journal Electronic Publishing House, 2015, Vo. 7 No. 2.

Big Data and Its Application in Management Innovation of Environmental Pollution Prevention and Control, China Academic Journal Electronic Publishing House, Environmental Protection vol. 44 No. Jun. 2016.

Cheng Chunming, et al., "Thinking on the Big Data Construction for Ecological Environment", 2015, Vo. 7 No. 6, China Academic Journal Electronic Publishing House.

Teng Jian-Ii, et al., "Development Status and Prospect of Environmental Monitoring Instrument Industry in China", China Environmental Protection Industry, Dec. 2017.

Peter Boeker, "Sensors and Actuators B 204", Elsevier, Jul. 27, 2014.

Mohammad Paknahad, et al., "On-Chip Electronic Nose for Wine Tasting: a Digital Microfluidic Approach", IEEE Sensors Journal, vol. 17, No. 14, Jul. 15, 2017.

JianCai Zhu, et al., "Evaluation of the synergism among volatile compounds in Oolong tea infusion by odour threshold with sensory analysis and E-nose", Food Chemistry 221 (2017) 1484-1490, Elsevier, Nov. 2, 2016.

Vania F. Pais, et al., "Using acoustic wave sensors to follow milk coagulation and to separate the cheeses according to the milk origin", Sensors and Actuators B 207 (2015) 1121-1128, Elsevier, Oct. 14, 2014.

Rohit Upadhyay, et al., "Electronic nose guided determination of frying disposal time of sunflower oil using fuzzy logic analysis", Food Chemistry 221 (2017) 379-385, Elsevier Oct. 21, 2016.

Shui Jiang, et al., "Internal quality detection of Chinese pecans (*Carya cathayensis*) during storage using electronic nose responses combined with physicochemical methods", Posthaverst Biology and Technology 118 (2016) 17-25, Elsevier, Mar. 26, 2016.

Wojciech Wojnowski, et al., "Electronic noses: Powerful tools in meat quality assessment" Meat Science 131 (2017) 119-131, Elsevier, May 6, 2017.

(56) References Cited

OTHER PUBLICATIONS

Philipp Schneider, et al., "Mapping urban air quality in near real-time using observations from low cost sensors and model information" Environment International 106 (2017) 234-247, Elsevier, Jun. 28, 2017.
Blanco-Rodriguez, Andy, et al., "Development of an electronic nose to characterize odours emitted from different stages in a wastewater treatment plant", Elsevier, Water Research 134, (2018), 92-100, Feb. 3, 2018.
Rens van de Goor, MD, et al., "Training and Validating a Portable Electronic Nose for Lung Cancer Screening", Journal of Thoracic Oncology, vol. 13 No. 5: 676-681, May 2018, Electronic Nose for Lung Cancer Screening.
Guillermo Suarez-Cuartin, et al., "Identification of Pseudomonas aeruginosa and airway bacterial colonization by an electronic nose in bronchiectasis" Respiratory Medicine 136 (2018) 111-117, Elsevier, Feb. 13, 2018.
Estefania Nunez Carmona, et al., "Detection of food and skin pathogen microbiota by means of anelectronic nose based on metal oxide chemiresistors", Sensors and Actuators B 238 (2017) 1224-1230, Elsevier, Sep. 16, 2016.
Su Aihua, et al., "Application of E-nose On-line Monitoring System in Landfill", Environment and Sustainable Development, No. 4, 2017.
The Chinese environmental protection soyuz, in November, China received 12,369 environmental protection reports, of which more than 50,000 were about air and noise pollution, Dec. 7, 2020.
J. Fonollosa, et al., "Calibration transfer and drift counteraction in chemical sensor arrays using Direct Standardization", Sensors and Actuators B 236 (2016) 1044-1053, Elsevier, May 18, 2016.
Wang Tong-jian, et al., "Comparative Analysis of Olfactometry Test Method of Odour Monitoring", Environmental Monitoring in China, vol. 29, No. 5, Oct. 2013.
S. De Vito, et al, "Calibrating chemical multisensory devices for real world applications:An in-depth comparison of quantitative machine learning approaches", Sensors and Actuators B 255 (2018) 1191-1210, Elsevier, Sep. 2, 2017.
Peter Andras, "High Dimensional Function Approximation With Neural Networks for Large Volumes of Data", IEEE Transactions on Neural Networks and Learning Systems, vol. 29, No. 2, Feb. 2018.
Yann LeCun, et al., Review Insight, "Deep Learning", Nature, Vo. 521, May 28, 2015.
British Standard, "Air quality—Determination of odour concentration by dynamic olfactometry", Apr. 2003.
Emission standards for odor pollutants, GB 14554-93, Jul. 19, 1993.
Air quality, odor measurement, three-point comparison odor bag method, GB/T 14675-93, Sep. 18, 1993.
Air quality Determination of three armour limbs Gas chromatography, GB/T 14676-93, Sep. 18, 1993.
Air quality Determination of toluene, xylene, styrene gas chromatography, GB/T 14677-1993, Oct. 27, 1993.
Air quality Determination of hydrogen sulfide, methyl mercaptan, methyl mercaptan and dimethyl disulfide gas chromatography, GB/T 14678-93, Sep. 18, 1993.
Air quality. Determination of hydrogen. Uranium hypochlorite-salicylic acid spectrophotometric Method, GB/T 14679-93, Sep. 18, 1993.
Air quality-Determination of carbon disulfide-diethyl rubber spectrophotometric method, GB/T 14680-93, Sep. 18, 1993.
Ambient air. Determination of sulfur dioxide. Formaldehyde absorption-pararosaniline spectrophotometric method, GB/T 15262-1994, Oct. 26, 1994.
Indoor air quality standards, GB/T 18883-2002, Nov. 19, 2002.
Technical specification for environmental monitoring of odor, HJ 905-2017, Dec. 29, 2017.

\* cited by examiner (a)

(b)

ONLINE CENTRALIZED MONITORING AND ANALYSIS METHOD FOR MULTI-POINT MALODOROUS GASES USING ELECTRONIC NOSE INSTRUMENT

CROSS-REFERENCE TO RELATED APPLICATIONS

This application is a United States national phase application of co-pending international patent application number PCT/CN2018/088913 titled "ONLINE MONITORING AND ANALYSIS METHOD FOR MALODOROUS GAS MULTI-POINT CENTRALIZED ELECTRONIC NOSE INSTRUMENT" and filed Mar. 30, 2018, which claims the benefit of and priority to Chinese patent application No. 201810471613.1 titled "Odor electronic nose instrument and online centralized monitoring method for multi-point malodorous gases" and filed May 17, 2018, and to Chinese patent application No. 201810471708.3 titled "Big-data-driven online centralized analysis method for multi-point malodorous gases using electronic nose instrument" and filed May 17, 2018, disclosures of all of which are incorporated herein by reference in their entireties.

TECHNICAL FIELD

The present disclosure relates to an online centralized monitoring and analysis system based on an electronic nose instrument for multi-point malodorous gases, generally relates to a monitoring method and an analytical instrument for meeting the market supervision requirements of environmental protection and management departments of the governments; for online monitoring and analysis requirements for malodorous pollution areas, including: (a) industrial parks, such as petrochemical, rubber, perfume, flavor, pharmaceutical, coating, brewing and paper making; (b) refuse and sewage treatment areas, such as refuse transfer, landfill and incineration, and sewage treatment; (c) farms; and (d) adjacent residential areas. The disclosure is specifically related to such technical fields as environmental protection, analytical chemistry, computer, artificial intelligence, big data, automatic control, precision measurement and others, aiming at solving the problems of automation, integration and miniaturization of electronic nose instruments, online monitoring and concentration prediction of various pollutants in the malodorous areas, and tracking and control of pollution sources.

BACKGROUND

At present, the main society contradiction in China is the contradiction between the people's growing needs for a better life and the unbalanced and inadequate development. Naturally, the environmental air pollutions and the needs for a better life are contradictory. Article 42 of the environmental protection law of the People's Republic of China, which came into force on Jan. 1, 2015, lists malodorous gases, exhaust gases, waste water, etc. as environmental pollutants and public hazards.

"Stink" refers to the unpleasant smells, which is a general term for all the smells that stimulate people's senses of smells, damage human's living environment, make people unbearable or unpleasant, sometimes called "peculiar odor". Malodorous pollutants refer to all malodorous substances in particular, and generally refer to all substances emitting odors. Malodorous pollutants widely exist in all enterprises with exhaust emission, including petrochemical industry, waste and sewage treatment, pharmaceutical industry, aquaculture and others as well as adjacent residential areas, with a wide distribution and a wide range of influence. The current situation of malodorous pollution in China is that there are many emission sources, complex malodorous components, lagging national standards and frequent complaints from residents.

In recent years, stink, as a kind of pollution disturbing people and endangering human health, has become a relatively prominent environmental pollution problem. With the improvement of people's living standards and the enhancement of environmental awareness, the proportion of malodorous pollution complaints in some countries or regions is on the rise. According to the incomplete statistics, malodorous complaints account for more than 50% of environmental complaints in the United States, 91.3% in Australia and tens of thousands in Japan every year. China is no exception. According to the People's Daily, in 2017, the national environmental protection reporting platform received 618, 856 reports[1]. Among them, air pollution is the most reported, accounting for 56.7%; malodorous/peculiar smell pollution is the most reported, accounting for 30.6%! That is to say, malodorous/abnormal smell pollution reports accounted for 17.35% of environmental protection reports in 2017.

The objects of assessment of malodorous pollutions are malodorous gases, and the assessment methods are divided into olfactory discrimination methods and instrumental analyzing methods. According to the Chinese National Standard GB14554-93 "Emission Standards for Malodorous Pollutants", the emission control indexes of malodorous pollutants include one qualitative dimensionless odor concentration, i.e., odor-unit (OU) value, and eight quantitative single-component concentrations, namely, $C_3H_9N$, $C_8H_8$, $H_2S$, $CH_4S$, $C_2H_6S$, $C_2H_6S_2$, $NH_3$ and $CS_2$. In addition, the Chinese National Standard GB/T18883-2002 "Indoor Air Quality Standard" specially recommends such two quantitative control indexes of $SO_2$ and total volatile organic compound (TVOC). At present, the evaluation index system of malodorous pollutions mainly consists of the above-mentioned 1 qualitative index and 10 quantitative indexes. According to GB14554-1993, the dimensionless concentration OU value is determined by the triangle malodorous bag method, the concentrations of $C_3H_9N$, $C_8H_8$, $H_2S$, $CH_4S$, $C_2H_6S$ and $C_2H_6S_2$ by the gas chromatography method, and the concentrations of $NH_3$ and $CS_2$ by the spectrophotometry method. According to the Chinese National Standard GB/T15262-94, the concentration of $SO_2$ is determined by the spectrophotometry method.

"Malodorous concentration" refers to the dilution of multiple malodorous samples collected on site, which are continuously diluted to the olfactory threshold by odorless clean air in the laboratory; European Standard EN17325-2003 uses the index of OU value to measure it. At present, the standard identification method of odor concentration mainly depends on the noses of sniffers[2]! This is true in many countries and regions, such as China, Europe, America, Japan, and South Korea. The Chinese National Standard GB/T14675-93 "Air quality—Determination of odor—Triangle odor bag method" which has been implemented for 25 years has standardized three links, i.e., selection of olfactory discriminator panel, collection of malodorous samples, artificial dilution and olfactory identification determination of malodorous samples. Europe, America, Australia, New Zealand and other countries use dynamic olfactometer to dilute the malodorous samples[3].

According to GB/T14675-1993 and the China environmental protection industry standard HJ905-2017, the malodorous samples shall be collected by the staff on site with sampling bottles or odorless bags (for example, the volume of each sampling bottle or each odorless bag is 10 L), transported back to the olfactory identification room, and then transferred to the odorless bags (for example, the volume of each odorless bag is 3 L) with syringes at a certain proportion, diluted with odorless clean air, and finally identified by the members of the olfactory panel. One of the core of the triangle comparison odor bag method is: after the malodorous sample is once diluted, one malodorous detector needs to smell three 3 L air bags, one of which is the diluted odor bag, the other two are odorless bags, from which the odor bag can be identified.

The right and wrong choice depends on the subjective judgment of the olfactory discriminators after sniffing". Although GB/T14675-1993 has been implemented for 25 years, the current situation is that many malodorous substances either have no olfactory thresholds, or the thresholds given by different countries or organizations are very different. In 2015, the National Key Laboratory for malodorous pollution control of environmental protection of Tianjin Academy of Environmental Sciences organized 30 olfactory discriminators (13 males and 17 females) to measure the olfactory thresholds of 40 kinds of malodorous substances. Table 1 shows the comparison of olfactory thresholds of 10 malodorous substances between China and Japan[4]. According to Table 1, the differences of olfactory thresholds between China and Japan are: 5 times for $NH_3$, nearly 3 times for $H_2S$, 28.12 times for trimethylamine $C_3H_9N$, 65.67 times for n-valeric acid $C_5H_{10}O_2$, etc. The above results manifest at least the following two problems: (1) the identification processes for determining dimensionless concentration OU values are very complex, and the costs of odor evaluations are very high; (2) the olfactory thresholds given by different countries or organizations are not objective and repetitive.

"Both I personally and the monitoring center are the victims of stenches. The stink of the landfill at the junction of Shenzhen and Huizhou was frequently complained by the surrounding people. Since last year (Note: 2016), we have to monitor once a month. The detection process is quite annoying every time. It takes 5 people to sample on site and 8 people to analyze in the laboratory. However, the results are hard to explain. Sometimes the scene is smelly, but the odor panel in the laboratory can't detect it out; sometimes the contrary. Now, the people are suing us and taking us to the court, and the government departments are not satisfied with us too. It's really a double whammy." Bentai WAN, the former chief engineer of the Ministry of Environmental Protection of the People's Republic of China, appealed[2], "Monitoring malodorous gases can't be performed by noses' smelling any more. It's like licking by tongue to identify whether or not a substance is poisonous. Isn't it fatal? It is very necessary for us to study the online automatic monitoring methods by using instruments, . . . ."

There are more than 4,000 kinds of malodorous components that can be felt by people's olfactory senses, among which dozens are harmful to human health, and the malodorous gases smelled in real life often contain dozens or hundreds of components[4]. For example, $H_2S$ gives off the smell of rotten eggs; amines gives off the smell of rotten fish; ammonia and aldehydes give off a pungent smell, and so on[5].

In the face of people's expectations for a better life, countries all over the world attach great importance to the treatment of environmental pollution. In recent years, the environmental protection departments in China attach great importance to online monitoring and treatment of malodorous gas pollutions[1,6-9], which is the basic requirement for building smart cities. According to "the 13$^{th}$ five-year development plan of China national environmental protection standard", the revised edition of GB14554-1993 and GB/T14675-1993 will be issued in 2019, as well as "the technical specifications for environmental monitoring of

TABLE 1

Comparison of olfactory thresholds of several malodorous substances in China and Japan (V/V, ppm)[4]

| Compound | $H_2S$ | $NH_3$ | $C_3H_9N$ | $C_5H_{10}O_2$ | $C_2H_6S_2$ | COS | $C_7H_8$ | $C_8H_{10}$ | $C_2H_5OH$ | $C_3H_8O$ |
|---|---|---|---|---|---|---|---|---|---|---|
| China | 0.0012 | 0.3 | 0.0009 | 0.0025 | 0.011 | 0.46 | 0.098 | 0.018 | 0.10 | 3.9 |
| Japan | 0.00041 | 1.5 | 0.000032 | 0.000037 | 0.0022 | 0.055 | 0.33 | 0.17 | 0.52 | 26 |
| Ratio | 2.93:1 | 1:5 | 28.12:1 | 65.67:1 | 5:1 | 8.36:1 | 1:3.37 | 1:9.44 | 1:5.2 | 1:6.67 |
| Odor characteristics | Rotten eggs | Stimulating odor | Fishy smell | Stink of sweat | Onion flavor | Rotten eggs | Aromatic odor | Aromatic odor | Alcohol taste | Alcohol taste |

Although the triangle comparative odor bag method specified in GB/T14675-1993 can reflect the feelings of ordinary people, its operability is very poor. The method requires a large number of sampling and odor detection panels to conduct an odor detection test, which costs a lot and is especially not suitable for odor detection of low-concentration or toxic substances[2,4-5]. The results of olfactory evaluation of the triangle comparative odor bag method are affected by many factors, such as (1) selection of sampling points on site; (2) sampling devices; (3) laboratory conditions; (4) capacity and state of olfactory discriminators; (5) odor concentration and initial dilution ratio; (6) olfactory time duration and fatigue. There are many limitations in the operation of artificial sampling, artificial dilution and artificial olfactory discrimination.

Wenshen XIAO, a senior engineer from Guangdong Environmental Monitoring Center of China, said emotionally[2]:

malodorous pollutants" and "the technical specifications for online monitoring of odors in ambient air and waste gases". We have noticed that the Chinese Industry Standard HJ905-2017 "Technical Specification for Odor Environmental Pollution Monitoring" has been released on Dec. 29, 2017 and officially implemented on Mar. 1, 2018.

Because the poor timeliness and high cost of olfactory identification methods and conventional instrument analyzing methods, and because the olfactory identification method is harmful to human bodies and the results of olfactory identification are not objective, the olfactory simulation methods, namely the electronic nose technologies and instruments, are particularly attractive[2,9].

Olfaction is a complex sensation of a large number of olfactory cells in the nasal cavity. The olfactory simulation method makes use of multiple gas sensors with overlapping performance to form an array to realize fast detection and qualitative and quantitative analysis of odors, which has attracted great attention[10]. For example, the electronic nose technology through the multiple perceptual responses of the gas sensor array to the odors, can determine the category, intensity, quality level, authenticity, freshness of the odorants, control their production processes, adjust the formulas and production processes, etc. The electronic nose method is now mainly used for the qualitative and quantitative analysis of complex odors, such as the qualities of wines[11], teas[12], milks[13], grains and oils[14]; the maturity of fruits[15]; the freshness of fishes and meat products[16]; the monitoring of water and ambient air[17-18]; disease diagnosis[19-20]; bacterial odor perception[21]; and so on.

Electronic nose technology has a broad application prospect. One of the development trends is to develop highly sensitive and highly selective gas sensors to achieve qualitative and quantitative detection and analysis of odors. It is encouraging that the sensitivity of some $S_nO_2$ semiconductor gas sensors has reached the $10^{-9}$ V/V (ppb) order of magnitude[10], which directly generate V-level voltage responses to odors without secondary amplification, and which is very attractive for online monitoring of malodorous pollutants. The second development trend is to use a number of different types of gas sensors with necessary sensitivity to form an array, focusing on the use of data analysis methods to improve the selectivity, to achieve the recognition, intensity estimation and key component prediction of many odors.

The relevant search results of theoretical and applied researches on electronic noses are as follows: (1) Literature. Before 1990, there were only more than 60 articles, and before 2000, there were more than 500 papers. Now there are more than 6,000 papers, which show that the electronic nose research has been widely carried out in recent years. (2) Patents. More than 500 international disclosure patents and more than 100 domestic disclosure patents are mostly published and granted in the past five years, which shows that the protection of intellectual property rights of olfactory simulation has been paid attention to. (3) Technical standards. There is no technical standard of product related to olfactory simulation in the ISO database. (4) Applications. Most of the work in China is carried out in the laboratory with the imported commercialized electronic noses[12, 15]. The FOX-type electronic nose made in French entered the Chinese market in 2007, which is very expensive (more than 1 million Yuan RMB), is mainly used for off-line laboratory detection, and is impossible to be used for the on-line detection of malodorous pollution processes. The above results show that the theory and application of olfactory simulation—electronic nose—are in urgent need of further study.

According to the ISI database, there are only 130 papers about the applications of electronic nose to the detection and analysis of environmental malodorous gases, less than 2% of the total. Most of them are off-line detection of indoor air, water and soil odor and data processing in laboratory. There is no report of online malodorous pollutant monitoring by electronic nose, and there is no mature odor electronic nose instrument[17-18].

The application of electronic noses for monitoring malodorous pollutions in China is in front of the world. Under the leadership of the environmental protection and management departments of the governments at all levels, some domestic emission units of pollution sources such as chemical parks, landfills and sewage treatment plants have adopted the commercialized electronic nose of the Airsense company of Germany and the alpha MOS company of France through bidding[22]. The arrays in these two products are composed of four metal oxide semiconductor (MOS), four electrochemistry (EC), and one photoionization detector (PID) gas sensors. They are specially developed for the Chinese market. In the actual application processes, there exist a series of problems, such as inconsistency in monitoring standards, inapplicability of analysis models, poor stability and consistency, high costs of equipment and operation. The odor monitoring system of Topo Zhixin company in China is composed of an array of 1 PID-type and 8 EC-type gas sensors, focusing on simple partial least squares (PLS) algorithm and data cloud transmission, trying to make a judgment based on the comparison between the tested samples and the standard samples, without considering the complexity of malodorous compositions and environmental variability[23].

The existing electronic nose monitoring systems adopt the mode of one monitoring point by one electronic nose, that is, "one point by one nose", which is obviously affected by the installation of monitoring cameras. There are some similar places between an electronic nose and a camera in function, but their use conditions are totally different. A series of problems will arise when the electronic nose is installed directly on the monitoring site: For example, the electronic nose instrument, especially the core components—multiple gas sensors, are exposed to the wind, sun and rain for a long time, which may affect their service life; the gas sensors are prone to the so-called fatigue and "poisoning" effect when exposed to the malodorous gases for long periods of time; the same type of gas sensors will generate consistency problems at different monitoring points; once installed, an electronic nose instrument will be difficult to move, and cannot change with the wind direction; over-dense distribution points not only affects the city appearance, but also have high cost; equipping with "zero gas" will lead to the huge volume and safety problems of instruments; the results of electronic nose instruments are different from the results of olfactory discrimination, gas chromatography and mass spectrometry, etc.

Shanghai Laogang landfill with 4 alpha MOS electronic noses and Tianjin Dagang Industrial Zone with 115 Airsense electronic noses costing 14.835 million [RMB still ranked the first and the third position in the environmental protection reporting number of times in 2017[24]. This fact fully shows that the so-called "odor electronic nose" is currently only a primary application at the sensor level.

In order to use electronic nose technology and instruments for online monitoring and analysis of malodorous gases, we must solve the following problems:

1. Design of Gas Sensor Array

The characteristics of malodorous gases are: (1) there are many and complex components. Except for a few inorganic substances such as $H_2S$, $NH_3$, $CS_2$ and $SO_2$, most of them are organic compounds, i.e., the so-called "volatile organic compounds (VOCs)"; (2) some malodorous substances have very low olfactory thresholds, but contribute a lot to malodorous concentrations; and vice versa; (3) some substances are non-toxic and harmless, contribute a little to malodorous concentrations, but the gas sensors are very sensitive to them.

Such factors as sensitivity, selectivity, response speed, stability, commercialization, miniaturization, service life, cost and others should be comprehensively considered in the selection of gas sensors. MOS-type gas sensors often have high sensitivity and other obvious advantages, but are not ideal in selectivity, so they should be the first choice of array components. Compared with MOS-type, EC-type gas sensors have the advantages of better selectivity, and the disadvantages are that their sensitivities are usually 1-2 orders of magnitude lower than the former, with a shorter service life (generally 1-2 years), a relatively large size, and a poor stability. EC-type gas sensors are mainly used for the detection of $H_2S$, $NH_3$, $CS_2$, $SO_2$ and other toxic gases[10, 22]. The characteristic of PID-type gas sensors is sensitivity to the VOCs between n-hexane and n-hexadecane, but that is not unique. The PID-type sensors have the disadvantages of large size, short life and high price. We should have a deep understanding of the performance and characteristics of different sensitive elements, design a small gas sensor array module, and solve the problems of poor long-term stability, noise elimination, temperature and humidity compensation, performance indifference replacement, etc.[25].

2. Standard Applicability and Consistency with Sensory and Conventional Instrument Analysis Results The Airsense and the alpha MOS electronic noses are based on the European Standard standard EN13725-2003. According to this standard, a dynamic olfactometer is used to continuously dilute the odors at any multiple (maximum $2 \times 10^6$ times), $0.04 \times 10^{-6}$ (V/V) n-butanol is used as the standard substance, and the function of the standard gas on human olfactory organs is designated as the basic unit of malodorous concentration, marked as $OU_E$, "the olfactory threshold of any mixed odor is equal to the stimulation amount of the standard gas to human", and the quantity value conforms to the ISO dimension system, with automatic test feature. The Chinese National Standard GB/T14675-1993 specifies a static manual test method, therefore its operability and scientificity are relatively bad, compared with the standard EN17325-2003[26].

The compositions and concentrations of odors are always changing. In the cases of poor selectivity of single gas sensor, how to transform the responses of gas sensor array into the results consistent with the analysis of conventional instruments such as malodorous concentration olfactometer and gas chromatographer/mass spectrometer is not only a theoretical problem involving computer and analytical chemistry, but also a practical problem involving the types of malodorous pollution sources[5].

3. Prediction of Dimensionless Odor Concentration and Multiple Key Component Concentrations Based on Big Data and Artificial Intelligence Human society is in the era of big data and artificial intelligence. The big data of health, financial, transportation, business, gene and others are profoundly changing people's life and work style. In China, the environmental big data has been put on the agenda, and the environmental protection management departments of the governments at all levels are vigorously promoting[7-8].

Because of the odor complexity and environmental variability, the small data and the conventional analysis methods are not enough to effectively establish a mathematical model for estimating and predicting various components of malodorous gases. If there is no big response data of the gas sensor arrays in the odor electronic nose instruments for a large number of on-site malodorous pollution tests, no laboratory sniffing data for a large number of malodorous samples by the sniffer panels, no off-line detection data for a large number of malodorous samples by conventional instruments such as gas chromatography/mass spectrometry, etc., it is impossible to estimate the odor concentrations and various pollutant components only by a single gas sensor array and a simple mathematical model. This is exactly what the Airsense and the alpha MOS electronic noses do, and the role of the monitoring data generated from that is very limited, or even untrustworthy.

Based on the response data of gas sensor arrays, olfactory identification data, analysis data of a conventional instrument such as a gas chromatograph/mass spectrometer, a spectrophotometer and others, we should establish the big data of malodorous gases, deeply study the theories and algorithms of artificial intelligence[27-29], and extract useful information such as the concentration of key components from the big odor data, so as to realize the real-time prediction of the above 10+1 control indexes of main malodorous pollutants by using an electronic nose instrument.

4. Integration, Automation and Intelligence of Odor Electronic Nose Instrument

There are many odor pollution sources, many malodorous components, various environmental changes, and many malodorous pollutant emission forms. We should abandon the "one point by one nose" distributed monitoring mode, study the optimization and fusion of gas sensor array, and modularization and miniaturization of multi-point centralized precise automatic sampling system. A new kind of odor electronic nose instrument with small size, light weight and easy operation should be developed by integrating the gas sensor array module, the automatic gas sampling module, the drive and control circuit module, and the computer into a test box; optimize the internal working conditions of the instrument, and deal with the external "ever-changing" with the internal "constant unchanged". An ideal situation is that the odor electronic nose instrument can realize simultaneous online monitoring of multiple monitoring points in a specific area (for example, within 4 $km^2$), i.e., fixed- or movable-point monitoring, of course, 24-hour continuous monitoring in month or even year. We should put forward some simple and effective machine learning models and algorithms to realize the 24-hour continuous estimation and prediction of the above 10+1 concentration control indexes of malodorous pollutants, and use wireless WIFI technique to transmit the measurement data and analysis results to the monitoring center and various terminals in real time, so as to realize the Internet-based remote control of malodorous pollutions.

REFERENCES

[1], Z. Yanhong, Ministry of environmental protection: More than 600,000 environmental protection reports were received, and nearly 60% of them were atmospheric reports, in 2017, People's Network (In Chinese), Jan. 23, 2018, hap://politics.people.com.cn/nl/2018/0123/c1001-29782203.html.

[2], D. Juan, Malodorous pollution only depends on nose? Experts suggest that 24-hour monitoring should be implemented as soon as possible, Guangzhou Daily (In Chinese), Jul. 6, 2016.

[3], L. Weifang, G. Jing, Z. Zengxiu, Y. Fengyue, Research survey and prospect of olfactory thresholds and mechanism of malodorous substances, Journal of Safety and Environment (In Chinese), 2015, 15(3): 327-330.

[4], W. Gen, Z. Zengxiu, G. Jing, H. Meng, L. Fulei, Testing and determination of the olfactory thresholds of 40 typical malodorous substances, Journal of Safety and Environment (In Chinese), 2015, 15(6): 348-351.

[5], W. Gen, Z. Zengxiu, H. Meng, J. Boyu, L. Fulei, M. Jie, Establishment and Application of Fingerprint of Malodorous Pollution Source, Research of Environmental Sciences (In Chinese), 2017, 30(12): 1944-1953.

[6], W. Jinnan, J Hongqiang, L. Nianlei, The strategic thinking on the 13th five-year plan of national environmental protection, Chinese Journal of Environmental Management (In Chinese), 2015, 7(2): 1-8.

[7], Z. Zhiming, Y. Wenjun, Big data and its application in management innovation of environmental pollution prevention and control, Environmental Protection (In Chinese), 2016, 06: 44-48.

[8], C. Chunming, L. Wei, S. Xu, Thinking on the big data construction for ecological environment, Chinese Journal of Environmental Management (In Chinese), 2015, 7(6): 9-13.

[9], T. Jianli, W. Yuhong, Development status and prospect of environmental monitoring instrument industry in China, China Environmental Protection Industry (In Chinese), 2017, 12: 19-24.

[10], P. Boeker, On 'Electronic Nose' methodology, Sensors & Actuators B: Chemical, 2014, 204: 2-17.

[11], M. Paknahad, A. Ahmadi, J. Rousseau, H. R. Nejad, M. Hoorfar, On-chip electronic nose for wine tasting: a digital microfluidic approach, IEEE Sensors Journal, 2017, 17(14): 4322-4329.

[12], J. C. Zhu, F. Chen, L. Y. Wang, Y. Niu, Z. B Xiao, Evaluation of the synergism among volatile compounds in Oolong tea infusion by odour threshold with sensory analysis and E-nose, Food Chemistry, 2017, 221: 1484-1490.

[13], V. F. Pais, M. I. S. Verissimo, J. A. B. P. Oliveira, et al., Using acoustic wave sensors to follow milk coagulation and to separate the cheeses according to the milk origin, Sensors & Actuators B: Chemical, 2015, 207: 1121-1128.

[14], R. Upadhyay, S. Sehwag, H. N. Mishra, Electronic nose guided determination of frying disposal time of sunflower oil using fuzzy logic analysis, Food Chemistry, 2017, 221: 379-385.

[15], S. Jiang, J. Wang, Internal quality detection of Chinese pecans (*Carya* cathayensis) during storage, Postharvest Biology & Technology, 2016, 118: 17-25.

[16], W. Wojnowski, T. Majchrzak, T. Dymerski, J. Gebicki, J. Namiesnik, Electronic noses: Powerful tools in meat quality assessment, Meat Science, 2017, 131: 119-131.

[17], P. Schneider, N. Castell, M. Vogt, F. R. Dauge, W. A. Lahoz, A. Bartonova, Mapping urban air quality in near real-time using observations from low-cost sensors and model information, Environment International, 2017, 106: 234-247.

[18], A. Blanco-Rodriguez, V. F. Camara, F. Campo, L. Becheran, A. R. Garcia-Ramirez, Development of an electronic nose to characterize odors emitted from different stages in a wastewater treatment plant, Water Research, 2018, 134: 92-100.

[19], R. V. D Goor, M. V. Hooren, A. M. Dingemans, B. Kremer, K. Kross, Training and validating a portable electronic nose for lung cancer screening, Journal of Thoracic Oncology, 2018, 13(5): 676-681.

[20], G. Suarez-Cuartin, J. Giner, J. L. Merino, A. Rodrigo-Troyano, O. Sibila, Identification of *Pseudomonas aeruginosa* and airway bacterial colonization by an electronic nose in bronchiectasis, Respiratory Medicine, 2018, 136: 111-117.

[21], E. N. Carmona, V. Sberveglieri, A. Ponzoni, et al., Detection of food and skin pathogen microbiota by means of an electronic nose based on metal oxide chemiresistors, Sensors & Actuators B: Chemical, 2017, 238: 1224-1230.

[22], S. Aihua, Z. Junjie, application of electronic nose in online odor monitoring system of landfill, Environment and Sustainable Development (In Chinese), 2017, 42(4): 129-131.

[23], G. Yonghui, F. Xilai, H. JinFang, G. Lihua, quantitative monitoring method of environmental malodorous pollution, China Invention Patent, No., 2013100985244, Authorized: Mar. 16, 2016 (In Chinese).

[24], The VOC Pollution Prevention and Control Committee of China Environmental Protection Federation, In November, more than 50,000 environmental protection reports were received, the most of which involved air and noise pollution, www.acef-vocs.com.cn/sv_view.aspx?FId=t8:36:8&Id=521&TypeId=36 (In Chinese).

[25], J. Fonollosa, L. Fernandez, A. Gutierrez-Galvez, R. Huerta, S. Marco, Calibration transfer and drift counteraction in chemical sensor arrays using Direct Standardization, Sensors & Actuators B: Chemical, 2016, 236: 1044-1053.

[26], W. Tongjian, T. Xiuhua, W. lin, Comparative Analysis of Olfactometry Test Method of Odour Monitoring, Environmental Monitoring in China (In Chinese), 2013, 29(5): 169-172.

[27], S. D. Vito, E. Esposito, M. Salvato, O. Popoola, F. Formisano, R. Jones, G. D. Francia, Calibrating chemical multisensory devices for real world applications: An in-depth comparison of quantitative machine learning approaches, Sensors & Actuators B: Chemical, 2018, 255(2): 1191-1210.

[28], A. Peter, High-dimensional function approximation with neural networks for large volumes of data, IEEE Transactions on Neural Networks and Learning Systems, 2018, 29(2): 500-508.

[29], Y. LeCun, Y. Bengio, G. Hinton, Deep learning, Nature, 2015, 521: 436-444.

SUMMARY

The disclosure is based on the existing disclosure patents: "Machine olfactory device and its olfactory simulation test method" (Chinese patent application No. 02111046.8); "Machine olfactory odor recognition method based on modular combined neural networks" (Chinese patent application No. 03141537.7); "Olfactory simulation instrument and qualitative and quantitative analysis method for multiple odors" (Chinese patent application No. 201010115026.2); "Multi-channel integrated olfactory simulation instrument and on-line analysis method of biological fermentation process" (Chinese patent application No. 201310405315.X). On the basis of the above-mentioned patent applications, an online centralized monitoring and analysis system based on an electronic nose instrument for multi-point malodorous gases is provided to solve the long-term online monitoring of multiple points in malodorous pollution areas and online prediction of multiple malodorous gas concentration control indexes.

In order to achieve the above purposes, the present disclosure is titled "online centralized monitoring and analysis system based on electronic nose instrument for multi-point malodorous gases". The online centralized monitoring and analysis system includes an odor electronic nose instrument (I), several gas sampling heads (II), an external vacuum pump (III), an ambient air purification device (IV), a clean air cylinder (V), gas pipelines, an electronic hygrometer (VI), a central control room (VII) and a plurality of stationary/mobile terminals (VIII), to realize the long-term cyclical monitoring of 10 malodorous pollution sites, and online estimation and prediction of multiple concentration control index values of malodorous pollutions in the specified pollution areas.

The odor electronic nose instrument (I) includes a gas sensor array and a thermostatic working room (I(a)) of the gas sensor array, a multi-point centralized auto-sampling system (I(b)), and a computer control and data analyzing system (1(c)). The thermostatic working room (I(a)) of the gas sensor array is comprised of a gas sensor array (I-1) and its annular working chamber, a thermal insulation layer (I-2), a resistance heating wire (I-3) and a fan (I-4). The gas sensor array (I-1) is comprised of 16 gas sensors, which are uniformly distributed in a sealed chamber having a middle diameter of 140 mm and a section size of 21 mm×17 mm, forming the annular working chamber. The thermostatic working room (I(a)) of the gas sensor array is with a constant temperature of 55±0.1° C. and located at the top right of the electronic nose instrument (I). The multi-point centralized auto-sampling system (I(b)) includes an internal miniature vacuum pump (I-14), 14 two-position two-port electromagnetic valves comprising a first two-position two-port electromagnetic valve (I-5), a second two-position two-port electromagnetic valve (I-6-1), a third two-position two-port electromagnetic valve (I-6-2), a fourth two-position two-port electromagnetic valve (I-6-3), a fifth two-position two-port electromagnetic valve (I-6-4), a sixth two-position two-port electromagnetic valve (I-6-5), a seventh two-position two-port electromagnetic valve (I-6-6), an eighth two-position two-port electromagnetic valve (I-6-7), a ninth two-position two-port electromagnetic valve (I-6-8), a tenth two-position two-port electromagnetic valve (I-6-9), an eleventh two-position two-port electromagnetic valve (I-6-10), a twelfth two-position two-port electromagnetic valve (I-8), a thirteenth two-position two-port electromagnetic valve (I-10), and a fourteenth two-position two-port electromagnetic valve (I-13), a throttle valve (I-11), a flowmeter (I-12), a vacuum pressure gauge (I-7), a gas buffer cavity (I-9), which are located at the lower right of the electronic nose instrument (I). The computer control and data analyzing system (I(c)) includes a computer mainboard (I-15), a data acquisition card (I-16), a monitor (I-17), a drive and control circuit module (I-18), a precision linear and switching power module (I-19), a hard disk, a network card, a video card, which are located on the left side of the electronic nose instrument (I).

The multi-point centralized auto-sampling system (I(b)) has a gas sampling period of $T_0$=180-300 s for a malodorous gas at a single monitoring point, with a default value $T_0$=240 s, so the gas sensor array (I-1) generates a 16-dimensional response vector for a specified monitoring point. According to the 16-dimensional response vector for a monitoring point, the computer control and data analyzing system (I(c)) uses the cascade machine learning model to perform real-time analysis and prediction of an olfactory concentration value of the malodorous gas (also referred to as a dimensionless concentration odor unit (OU) value), concentrations of eight compounds specified in GB14554-1993 and concentrations of $SO_2$ and the total volatile organic compound specified in GB/T18883-2002, which include 10+1 gases in total; and finally transmitting monitoring data and prediction results to the central control room (VII) and designated stationary/mobile terminals (VIII) through wireless Internet; where the eight compounds are $NH_3$, $H_2S$, $CS_2$, $C_3H_9N$, $CH_4S$, $C_2H_6S$, $C_2H_6S_2$ and $C_8H_8$.

The electronic nose instrument (I) obtains a 16-dimensional response vector every single gas sampling period $T_0$, which is stored in a data file of the computer hard disk. 10 two-position two-port electromagnetic valves from the second two-position two-port electromagnetic valve (I-6-1) to the eleventh two-position two-port electromagnetic valve (I-6-10) are used to control on-and-off of malodorous gases at 10 monitoring points in turn within the maximum 4 km² area, the online measurement of malodorous gases at 10 monitoring points is realized by the cyclic gas sampling period of T=10×$T_0$, and the monitoring data are stored in 10 data files, which are the numerical basis for the electronic nose instrument (I) to realize the cyclically online quantitative prediction of 10+1 concentration control index values of malodorous gases.

The single gas sampling period $T_0$ includes the following five stages: initial recovery of the gas sensor array (I-1) lasting 95-215 s, accurate calibration of clean air lasting 30 s, balance lasting 5 s, malodorous gas headspace sampling lasting 30 s and purified ambient air flushing lasting 20 s. In the single gas sampling period $T_0$, under the control of the computer, a two-position two-port electromagnetic valve (I-6-k), k=1, 2, . . . , 10 at the corresponding to the single monitoring point is turned on, while the nine two-position two-port electromagnetic valves (I-6-(~k)) corresponding to the other nine monitoring points are disconnected. The internal miniature vacuum pump (I-14) sucks in the malodorous gas in the gas buffer cavity (I-9) with a flow rate of 1,000 ml/min thereby enabling the malodorous gas to flow through the annular working chamber of the gas sensor array (I-1) and skim over surfaces of the sensitive films of the gas sensors, so that the gas sensor array (I-1) generates sensitive responses for 30 s. Since the beginning of the balance state, the computer control and data analyzing system (I(c)) continuously records the sensitive response data, including the 45 s response data of the gas sensor array (I-1) in the following three stages: a balance stage of 5 s, a malodorous gas headspace sampling stage of 30 s, and a purified ambient air flushing stage of the first 10 s, which are temporarily stored in a text file. The response data of other time slots in the single gas sampling period $T_0$ are not recorded.

In the 45 s-long response data, the difference between a steady-state maximum value and the minimum value of the response curve of a single gas sensor is extracted as a response component, so that the gas sensor array (I-1) generates a 16-dimensional response vector. In the 10 s after the end of the data recording, that is, the $2^{nd}$ 10 s of the purified ambient air flushing stage, the computer control and data analyzing system (I(c)) predicts the 10+1 malodorous pollutant concentration control index values based on the 16-dimensional response vector.

The gas sensor array (I-1) is comprised of 11 metal oxide semiconducting (MOS) elements, 4 electrochemical (EC) and 1 photo ionization detector (PID). Among them, the 11 MOS elements are used to detect a variety of organic/inorganic compounds; the 4 EC elements are configured to detect the 4 inorganic compounds: $NH_3$, $H_2S$, $CS_2$ and $SO_2$; and the single PID element is employed to detect TVOCs.

The online centralized monitoring and analysis system is operable to realize online monitoring and analysis of multi-point malodorous gases in a certain specific area either as large as several square kilometers, or as small as a production workshop, a building, and even one point. 10 monitoring points are set in a maximum area of 2 km*2 km=4 km², including 9 stationary points and 1 mobile point. The electronic nose instrument (I) is located indoor, which connects each monitoring point through a stainless steel pipe with an inner diameter of ϕ10 mm. Each gas sampling head is in the form of water tap, is connected to a commercial dedusting, dehumidification and purification part, and is installed or moved to the designated position. To change the position of a monitoring point, the operator only needs to re-lay the stainless steel pipe, to re-install and re-move the gas sampling head to the designated position, high or low, upstairs or downstairs, just like laying a water pipe or a cable.

Eight or more monitoring points are arranged around a boundary of a specified area, and the target is to make the stainless steel pipelines between the electronic nose instrument (I) and 10 monitoring points be the shortest. For a chemical industrial park, a residential area and other areas with accessible paths, the electronic nose instrument (I) is arranged indoor in the center of the area. For a landfill, a sewage treatment plant and other areas without accessible paths, the electronic nose instrument (I) is arranged indoor at a boundary of the area.

The external vacuum pump (III) has a suction rate of 250-280 l/min, a limit vacuum degree of 100-120 mbar, and is operative to work continuously for a long period of time. The malodorous gas at a monitoring point with a linear distance of 2.5 km is operative to be pumped into the electronic nose instrument (I) through a stainless steel pipe of a $\phi 10$ mm inner diameter in less than 1 min. In the single gas sampling period $T_0$, except for the 30 s headspace sampling stage, the malodorous gas pumped into the electronic nose instrument (I) in the other stages does not flow through the annular working chamber of the gas sensor array (I-1), but is directly discharged to outdoor.

The gas buffer cavity (I-9) with a size of $\phi 40$ mm*5 mm is set inside the electronic nose instrument (I). The flow rate of the malodorous gas measured here is 16 times lower than that at the stainless steel pipe with an inner diameter of $\phi 10$ mm. Only at the 30 s headspace sampling stage, the internal miniature vacuum pump (I-14) draws the malodorous gas in the gas buffer cavity (I-9) into the annular working chamber of the gas sensor array, such that the gas sensor array (I-1) produces a sensitive response. The internal miniature vacuum pump (I-14) always sucks fresh malodorous gases.

Before the headspace sampling of malodorous gas, the 30 s accurate calibration stage of 1,000 ml/min clean air makes multiple perceptions of the malodorous gas of the gas sensor array (I-1) on the same baseline. The standard volume of 12-15 MPa compressed clean air cylinder (V) is 40 L, and the volume converted to normal temperature and pressure is 6 m³. When the single gas sampling period $T_0=3$, 4 and 5 minutes, a bottle of 40 L compressed clean air is used for 25, 33 and 41 days, respectively. The outdoor ambient air where the electronic nose instrument (I) is located at is first purified by an ambient air purification device (IV), and then is used to flush the gas sensor array (I-1), so as to primarily restore the gas sensor array to the reference state and reduce the operation cost.

The odor big data includes: (1) The online detection data by the gas sensor array (I-1) for a large number of malodorous pollutants on chemical industrial parks including fragrance and flavor factories, pharmaceutical factories, landfill sites, sewage treatment plants, farms and neighboring residential areas. (2) The off-line laboratory test data by the gas sensor array (I-1) for a large number of headspace volatile gases of standard malodorous samples, including 5 standard odorants specified in GB/T14675-1993, i.e., β-phenylethanol, isovaleric acid, methylcyclopentanone, peach aldehyde and β-methylindole; the standard malodorous samples made up of nine single-component malodorous pollutants with different concentrations designated by GB14554-1993: $C_3H_9N$, $C_8H_8$, $H_2S$, $CH_4S$, $C_2H_6S$, $C_2H_6S_2$, $NH_3$, $CS_2$, and $SO_2$ by GB/T18883-2002, as well as standard malodorous samples of mixed components prepared with different concentrations of multiple single compounds. (3) The off-line panel evaluation data of dimensionless concentration OU values specified in GB/T14675-1993 and HJ 905-2017 for the malodorous gases sampled by the vacuum bottles or bags at a large number of malodorous sites and immediately transported back to the olfactory rooms. (4) The off-line TVOC data by gas chromatography, and off-line $SO_2$ data obtained by spectrophotometry, depending upon the malodorous pollutants in GC adsorption tubes sampled on sites according to GB/T18883-2002. (5) The off-line laboratory test data of 8 malodorous components specified in the Chinese National Standards from GB/T14676-1993 to GB/T14680-1993 by gas chromatography, mass spectrometry and spectrophotometry for the on-site sampling malodorous pollutants. (6) The residents' complaint data in the vicinities of malodorous pollution sources.

The electronic nose instrument (I) uses the cascade machine learning model to predict the dimensionless concentration OU value and multiple specified concentration control index values of malodorous pollutants at the time points of t+1, t+2 and t+3 in the near future; the first level of the cascade machine learning model, i.e., the convolutional neural network (CNN) layer, is responsible for predicting the responses of the gas sensor array (I-1) to the malodorous gases at the time points of t+1, t+2 and t+3, based on the occurred time-series responses of the gas sensor array (I-1) at the current time t and the recent past; the second level of the cascade machine learning model, i.e., the deep neural network (DNN) layer, further predicts the dimensionless concentration OU value and multiple specified concentration control index values of various malodorous gases at the time points of t+1, t+2 and t+3, based on the long-term accumulation of malodorous gas big data and the prediction values of the first-level, i.e., the convolution neural network layer.

According to the "divide-and-conquer" strategy, the first level of the cascade machine learning model uses 16*3 groups of single-output single-hidden-layer convolution neural networks to predict the responses of every gas sensor at the time points of t+1, t+2 and t+3. For the single period of $T_0=4$ minutes, it is equivalent to predicting the responses at 40, 80 and 120 minutes in the coming future from the current time t.

Let the three single-output single-hidden-layer convolution neural network modules with a single period of $T_0=4$ minutes predict the responses of the gas sensor i at the time points of t+1, t+2 and t+3, respectively:

(a), A single-output single-hidden-layer convolution neural network $CNN_{i1}$ predicts the response of the gas sensor i at the time point of t+1:

If the convolutional neural network $CNN_{i1}$ is used to learn the 18 time-series response data of the gas sensor i that have occurred before the time t, the delay length $\Delta t=9$, then the number of input nodes is $m_i=9$, the number of hidden nodes is $h_i=5$, and the number of output nodes is $n_i=1$.

The preprocessed time-series response data set $X_{i1}$ of the gas sensor i learned online by convolutional neural network $CNN_{i1}$ is:

$$X_{i1} = \begin{pmatrix} x_i(t-9) & x_i(t-8) & x_i(t-7) & x_i(t-6) & x_i(t-5) \\ x_i(t-4) & x_i(t-3) & x_i(t-2) & x_i(t-1) & \\ x_i(t-10) & x_i(t-9) & x_i(t-8) & x_i(t-7) & x_i(t-6) \\ x_i(t-5) & x_i(t-4) & x_i(t-3) & x_i(t-2) & \\ & & \cdots & & \\ x_i(t-17) & x_i(t-16) & x_i(t-15) & x_i(t-14) & x_i(t-13) \\ x_i(t-12) & x_i(t-11) & x_i(t-10) & x_i(t-9) & \\ x_i(t-18) & x_i(t-17) & x_i(t-16) & x_i(t-15) & x_i(t-14) \\ x_i(t-13) & x_i(t-12) & x_i(t-11) & x_i(t-10) & \end{pmatrix} \in R^{10 \times 9}$$

The target output is:

$d_{i1} = (x_i(t) x_i(t-1) x_i(t-2) x_i(t-3) x_i(t-4) x_i(t-5) x_i(t-6) x_i(t-7) x_i(t-8) x_i(t-9))^T \in R^{10}$

This approach is equivalent to the convolutional neural network $CNN_{i1}$ to learn a set of 18 time-series responses of the gas sensor i that have occurred in the last 12 hours, generating 10 9-dimensional time-series response samples, that is, the number of samples is $N_{i1} = 10$. The activation functions of hidden and output layers in the $CNN_{i1}$ are the modified Sigmoid function $f(\varphi) = 3/(1 + \exp(-\varphi/3))$, and the learning factor is $\eta_i = (5/N_{i1}) = 0.2$. The data set $X_{i1}$ and the target output $d_{i1}$ are transformed to the range of [0, 3].

After the online learning in 10 seconds, the convolutional neural network $CNN_{i1}$ depends upon a 9-d time-series response in the latest time period to predict the response $x_i(t+1)$ of the gas sensor i at the time point of t+1. When $T_0 = 4$ minutes, it is equivalent to predicting the response of the gas sensor i in the next 40 minutes, where the 9-d time-series response in the latest time period is as follows:

$x_{i1} = (x_i(t-8) x_i(t-7) x_i(t-6) x_i(t-5) x_i(t-4) x_i(t-3) x_i(t-2) x_i(t-1) x_i(t))^T \in R^9$ (b), Two single-output single-hidden-layer convolution neural networks $CNN_{i2}$ and $CNN_{i3}$ predict the responses of the gas sensor i at the time points of t+2 and t+3:

The structures of convolutional neural networks $CNN_{i2}$ and $CNN_{i3}$ are still $m_i = 9$, $h_i = 5$, $n_i = 1$; and the preprocessed data sets $X_{i2}$ and $X_{i3}$ online learned are respectively:

$$X_{i2} = \begin{pmatrix} x_i(t-10) & x_i(t-9) & x_i(t-8) & x_i(t-7) & x_i(t-6) \\ x_i(t-5) & x_i(t-4) & x_i(t-3) & x_i(t-2) & \\ x_i(t-11) & x_i(t-10) & x_i(t-9) & x_i(t-8) & x_i(t-7) \\ x_i(t-6) & x_i(t-5) & x_i(t-4) & x_i(t-3) & \\ & & \cdots & & \\ x_i(t-18) & x_i(t-17) & x_i(t-16) & x_i(t-15) & x_i(t-14) \\ x_i(t-13) & x_i(t-12) & x_i(t-11) & x_i(t-10) & \\ x_i(t-19) & x_i(t-18) & x_i(t-17) & x_i(t-16) & x_i(t-15) \\ x_i(t-14) & x_i(t-13) & x_i(t-12) & x_i(t-11) & \end{pmatrix} \in R^{10 \times 9}$$

and $$X_{i3} = \begin{pmatrix} x_i(t-11) & x_i(t-10) & x_i(t-9) & x_i(t-8) & x_i(t-7) \\ x_i(t-6) & x_i(t-5) & x_i(t-4) & x_i(t-3) & \\ x_i(t-12) & x_i(t-11) & x_i(t-10) & x_i(t-9) & x_i(t-8) \\ x_i(t-7) & x_i(t-6) & x_i(t-5) & x_i(t-4) & \\ & & \cdots & & \\ x_i(t-19) & x_i(t-18) & x_i(t-17) & x_i(t-16) & x_i(t-15) \\ x_i(t-14) & x_i(t-13) & x_i(t-12) & x_i(t-11) & \\ x_i(t-20) & x_i(t-19) & x_i(t-18) & x_i(t-17) & x_i(t-16) \\ x_i(t-15) & x_i(t-14) & x_i(t-13) & x_i(t-12) & \end{pmatrix} \in R^{10 \times 9}$$

That is to say, $X_{i2}$ and $X_{i3}$ also have ten 9-d time-series response samples, and have the same number of samples $N_{i2} = N_{i3} = N_{i1} = 10$; the target outputs and the depended time-series responses of $CNN_{i2}$ and $CNN_{i3}$ are similarly to that of $CNN_{i1}$; when $T_0 = 4$ minutes, it is equivalent to learning the responses of the gas sensor i in the 12 hours before 40 and 80 minutes, to predicting the responses $x_i(t+2)$ and $x_i(t+3)$ of the gas sensor i in the time points of t+2 and t+3, respectively, and to predicting the responses of the gas sensor i in the next 80 and 120 minutes.

According to the "divide-and-conquer" strategy, 10+1 concentration control index values of malodorous gases, including $NH_3$, $H_2S$, $CS_2$, $C_3H_9N$, $CH_4S$, $C_2H_6S$, $C_2H_6S_2$, $C_8H_8$, $SO_2$, TVOC and dimensionless strength OU value, are divided into 11 single concentration prediction problems. In the second level of the cascade machine learning model, 10+1 single-output three-hidden-layer deep neural network modules are used to predict the 10+1 malodorous concentration control index values. The training set of a single-output deep neural network is the big data online detected by the gas sensor array (I-1) of the odor electronic nose instrument (I) for the standard malodorous liquid/gas samples and a large number of malodorous pollutants. The target outputs are the malodorous olfactory values, off-line measurement values of conventional instruments such as gas chromatographer, mass spectrometer and spectrophotometer, and the data of residents' complaints.

Each single-output three-hidden-layer deep neural network $DNN_j$ adopts the bottom-up off-line learning manner. The parameters of the first and the second hidden layers are determined by the single-hidden-layer peer-to-peer neural networks, namely, the weights of the hidden-to-output layer are directly equal to the weights of the input-to-hidden layer, the target outputs are directly equal to the input values of the peer-to-peer network, and the input and the output components are proportionally transformed to the range of [0, 3]. The activation functions of hidden units of each single-hidden-layer peer-to-peer neural network are the modified sigmoid functions $f(\varphi) = 3/(1 + \exp(-\varphi/3))$, the error back-propagation algorithm is adopted, the learning factor is $\eta_j = 1/N_j$, and the hidden-to-output layer is discarded after learning, where $N_j$ is the number of samples in the odor big data.

The $j^{th}$ single-output deep neural network $DNN_j$ depends on the predicted responses of 16 convolutional neural networks to the gas sensor array (I-1) at the time point of t+1, $\{x_1(t+1), x_2(t+1), \ldots, x_{16}(t+1)\}$, to predict the $j^{th}$ concentration index value $y_j(t+1)$ of odor at the time point of t+1. Similarly, the $DNN_j$ depends on the predicted responses of 16 convolutional neural networks, $\{x_1(t+2), x_2(t+2), \ldots, x_{16}(t+2)\}$ and $\{x_1(t+3), x_2(t+3), \ldots, x_{16}(t+3)\}$, to predict the $j^{th}$ concentration index values $y_j(t+2)$ and $y_j(t+3)$ of odor at the time points of t+2 and t+3, respectively.

If the actual input is the current response vector of the gas sensor array, $x(t) = (x_1(t), x_2(t), \ldots, x_{16}(t))^T$, and the temperature and humidity values at the time t are added if necessary, then the actual output of $DNN_j$ is the estimation of the current concentration value $y_j(t)$ of malodorous component j.

The odor electronic nose instrument (I) used for long-term online monitoring of multiple monitoring points and online prediction of various concentration control index values of malodorous gases in the pollution areas include the following operations:

(1), a power on operation: preheat the instrument for 30 minutes; click the "Air purifier on" option on the screen menu, and the ambient air purification device (IV) starts to clean the indoor air where the odor electronic nose instrument (I) is located at, and works continuously for a long time until the operator clicks the "Air purifier off" option;

Under the suction action of the internal miniature vacuum pump (I-14), the purified ambient air sequentially flows through the two-position two-port electromagnetic valve (1-5), the annular working chamber of the gas sensor array (I-1) and the thirteenth two-position two-port electromagnetic valve (I-10) with a flow rate of 6,500 ml/min, and then is discharged to outdoor; the temperature in the annular working chamber of the gas sensor array (I-1) reaches a constant 55±0.1° C. from the room temperature.

Click the "External vacuum pump on" option in the screen menu; the external vacuum pump (III) with a suction flow rate of 250-280 l/min and a limit vacuum degree of 100-120 mbar sucks in the odor from a monitoring point with a linear distance of up to 2.5 km to the odor electronic nose instrument (I) within 1 minute through a stainless steel pipe with an inner diameter of ϕ10 mm, and then forces the odor to flow through the corresponding two-position two-port electromagnetic valve (I-6-$k$), k=1, 2, ..., 10, the vacuum pressure gauge (I-7) and the gas buffer cavity (I-9), and then directly discharges the odor to the outdoor. The external vacuum pump (III) continuously sucks in the malodorous gas until the operator clicks the "external vacuum pump off" option on the screen menu.

Modify the setting of "Single sampling period $T_0$" in the screen menu, with the default value $T_0$=4 minutes. The cycle sampling period of malodorous gases for 10 monitoring points is $T=10T_0$.

(2), an operation for starting the cyclic sampling period of malodorous gases: the "Start detection" button on the screen menu is clicked, the odor electronic nose instrument (I) conducts the cyclic monitoring operation on 10 monitoring points in turn, and the computer control and data analyzing system (I(c)) automatically generates 10 text files in the designated folder to store the response data of the gas sensor array (I-1) to the malodorous gases at 10 monitoring points.

(3), an operation for starting the single sampling period of malodorous gas for the monitoring point k (=1, 2, ..., 10) is started. $T_0$=4 minutes is taking as an example:

(3.1), a preliminary recovery operation of the gas sensor array: In the 0-155 s of the single gas sampling period $T_0$, under the suction action of the internal miniature vacuum pump (I-14), the purified ambient air sequentially flows through the first two-position two-port electromagnetic valve (I-5), the annular working chamber of the gas sensor array (I-1), the thirteenth two-position two-port electromagnetic valve (I-10) with a flow rate of 6,500 ml/min, and then is discharged to the outdoor. Under the action of the 6,500 ml/min purified ambient air, the accumulated heat in the annular working chamber of the gas sensor array (I-1) is taken away, the odor molecules adhered to the sensitive membrane surfaces of the gas sensor array and the inner wall of the pipelines are preliminarily washed away, and the gas sensor array (I-1) is preliminary restored to the reference state, lasting 155 s.

Among 10 two-position two-port electromagnetic valves from the second two-position two-port electromagnetic valve (I-6-1) to the eleventh two-position two-port electromagnetic valve (I-6-10), only a two-position two-port electromagnetic valve (I-6-$k$) is on, the other nine two-position two-port electromagnetic valves are off, and the external vacuum pump (III) draws the malodorous gas in the monitoring point k (=1, 2, ..., 10) into the odor electronic nose instrument (I).

(3.2), an accurate calibration operation of the gas sensor array by clean air: In the 156-185 s range of the single gas sampling period $T_0$, the fourteenth two-position two-port electromagnetic valve (I-13) is on, the first two-position two-port electromagnetic valve (I-5), the twelfth two-position two-port electromagnetic valve (I-8) and the thirteenth two-position two-port electromagnetic valve (I-10) are off, and the ten two-position two-port electromagnetic valves from the second two-position two-port electromagnetic valve (I-6-1) to the eleventh two-position two-port electromagnetic valve (I-6-10) maintain the state of the step (3.1). Under the suction action of the internal miniature vacuum pump (I-14), the clean air flows through the fourteenth two-position two-port electromagnetic valve (I-13), the gas pipelines, the annular working chamber of the gas sensor array (I-1), the throttle valve (I-11), the flowmeter (I-12) and the internal miniature vacuum pump (I-14) with the flow rate of 1,000 ml/min, and then is discharged out of the room. The clean air makes the gas sensor array (I-1) accurately return to the reference state; the external vacuum pump (III) continues to draw, which lasts 30 s.

(3.3), an operation of a balance stage: In the 186-190 s segment of the single gas sampling period $T_0$, the first two-position two-port electromagnetic valve (I-5), the twelfth two-position two-port electromagnetic valve (I-8), the thirteenth two-position two-port electromagnetic valve (I-10) and the fourteenth two-position two-port electromagnetic valve (I-13) are disconnected, and ten two-position two-port electromagnetic valves from the second two-position two-port electromagnetic valve (I-6-1) to the eleventh two-position two-port electromagnetic valve (I-6-10) maintain the state of the step (3.1). There is no gas flow in the annular working chamber of the gas sensor array (I-1). From the $186^{th}$ second of the single gas sampling period $T_0$, i.e., the beginning of the balance state, the computer control and data analyzing system (I(c)) starts to record the real-time response data of the gas sensor array (I-1), and stores them in the designated temporary text file "temp.txt". The external vacuum pump (III) keeps drawing, which lasts 5 s.

(3.4), a headspace sampling operation of malodorous gas at the monitoring point k: In the 190-220 s segment of the single gas sampling period $T_0$, the twelfth two-position two-port electromagnetic valve (I-8) is on, the first two-position two-port electromagnetic valve (I-5), the thirteenth two-position two-port electromagnetic valve (I-10) and the fourteenth two-position two-port electromagnetic valve (I-13) are off, and ten two-position two-port electromagnetic valves from the second two-position two-port electromagnetic valve (I-6-1) to the eleventh two-position two-port electromagnetic valve (I-6-10) maintain the state of the step (3.1). Under the suction of the internal miniature vacuum pump (I-14), the malodorous gas in the gas buffer cavity (I-9) sequentially flows through the annular working chamber of the gas sensor array (I-1), the throttle valve (I-11), the flowmeter (I-12), the internal miniature vacuum pump (I-14) with a flow rate of 1,000 ml/min, and is finally discharged to outdoor. The sensitive responses of the gas sensor array (I-1) are recorded in the temporary file "temp.txt". The external vacuum pump (III) continues to draw, which lasts 30 s.

(3.5), a flushing operation of the gas sensor array: In the 221-230 s of the single gas sampling period $T_0$, the first two-position two-port electromagnetic valve (I-5) and the thirteenth two-position two-port electromagnetic valve (I-10) are connected, and the twelfth two-position two-port electromagnetic valve (I-8) and the fourteenth two-position two-port electromagnetic valve (I-13) are disconnected.

Under the suction action of the internal miniature vacuum pump (I-14), the purified ambient air sequentially flows through the first two-position two-port electromagnetic valve (I-5), the annular working chamber of the gas sensor array (I-1) and the thirteenth two-position two-port electromagnetic valve (I-10) with a rate of 6,500 ml/min, and then is discharged to outdoor. At the same time, among the 10 two-position two-port electromagnetic valves from the second two-position two-port electromagnetic valve (I-6-1) to the eleventh two-position two-port electromagnetic valve (I-6-10), if k<10, a two-position two-port electromagnetic valve ((I-6-(k+1))) is on, the other nine two-position two-port electromagnetic valves are off, and the external vacuum pump (III) turns to suck in the malodorous gas at the monitoring point (k+1); if k=10, let k+1=1, turns to the next sampling cycle of odor, and the external vacuum pump (III) turns to suck in the malodorous gas at the monitoring point k=1. Due to the role of the purified ambient air, the heat accumulated in the annular working chamber of the gas sensor array (I-1) is taken away, the odor molecules adhering to the sensitive film surfaces of the gas sensor array (I-1) and the inner walls of the pipelines are preliminarily washed away, and the gas sensor array (I-1) gradually returns to the reference state, which takes 20 seconds.

(a), In the 221-230 s of the single gas sampling period $T_0$, the response data of the gas sensor array continue to be recorded in temporary file "temp.txt" for a continuous period of 10 seconds. At the end of $230^{th}$ second, the computer control and data analyzing system (I(c)) stops recording the response data of the gas sensor array.

(b), In the 231-240 s of the single gas sampling period $T_0$, the computer control and data analyzing system (I(c)) performs the following three operations:

(b.1), Feature extraction: starting from the $231^{st}$ second, the maximum and the minimum steady-state response values of each gas sensor with a time duration of 45 seconds are extracted from the temporary file "temp.txt", the difference between the maximum and the minimum response value is taken as the characteristic response component $x_i(t)$ (i=1, 2, ..., 16) of each gas sensor to the malodorous gas at the monitoring point k at the current time t, and is recorded in the corresponding data file.

(b.2), Response prediction of the gas sensor array: The first level of the cascade machine learning model, namely 16*3 convolutional neural networks, is operative to realize online self-learning according to the time-series response vectors of the gas sensor array that have occurred before the current time t, i.e., the three time segments of [t−18, t], [t−19, t−1] and [t−20, t−2], and predicts the coming responses of the gas sensor array (I-1) at the future time points of $T_0$, 2T0 and $3T_0$.

(b.3), Prediction of concentration control index values of a malodorous gas: The second level of the cascade machine learning model, namely 10+1 deep neural networks, further predicts the 10+1 concentration control index values of the malodorous gas at the monitoring point k according to the response values of the gas sensor array predicted by the 16*3 convolution neural networks in the first level of the cascade machine learning model, which is showed on the monitor, and the monitoring and prediction results are transmitted to the central control room (VII) and multiple stationary/mobile terminals (VIII) through the Internet network.

(3.6), an ending operation the single sampling period of the malodorous gas at the monitoring point k: Return to the step (3.1), the single sampling cycle of a malodorous gas is at a monitoring point (k+1) starts. If k+1>10, the monitoring point k=1 of the next sampling cycle of malodorous gas starts.

Repeat the steps (3.1)~(3.6); the odor electronic nose instrument (I) is operative to realize cyclically online measurement, identification and prediction of 10+1 concentration control index values of malodorous gases at 10 monitoring points.

DETAILED DESCRIPTION

The detailed description of the present disclosure is further given below in conjunction with the above drawings.

Figure 1:
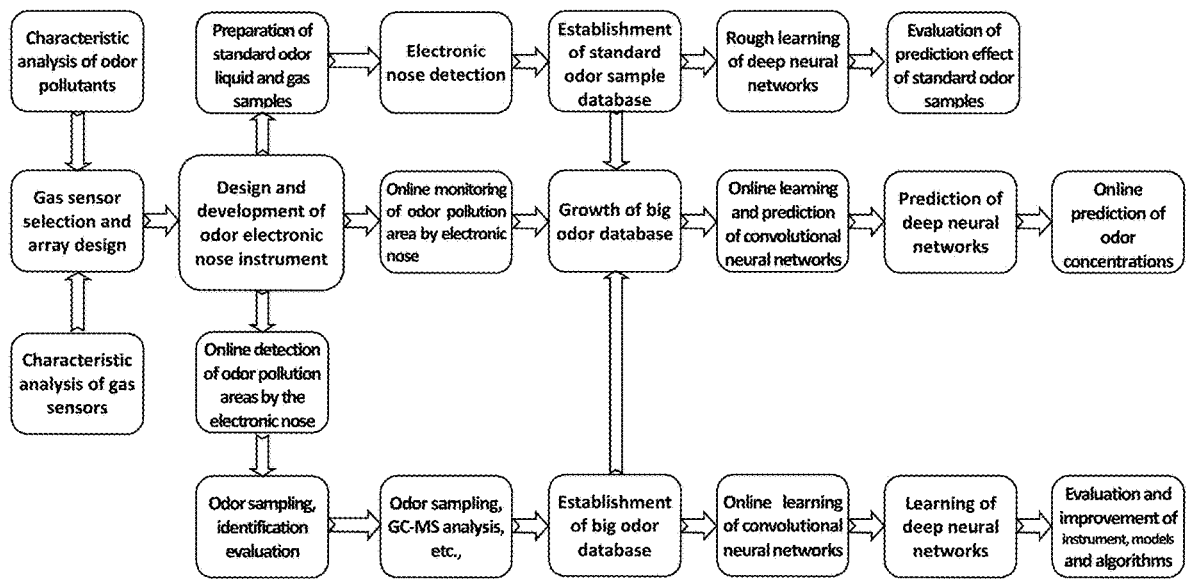
FIG. 1 illustrates a block diagram of the relationship among odor electronic nose instrument development, cascade machine learning model and algorithm, and online detection and prediction of malodorous pollutants according to the present disclosure named an online centralized monitoring and analysis system based on an electronic nose instrument for multi-point malodorous gases.

FIG. 1 is a block diagram illustrating the relationship of odor electronic nose instrument development, cascade machine learning model and algorithm, and online detection and prediction of malodorous pollutants.

The disclosure first analyzes the characteristics of malodorous pollutants and gas sensors from the chemical and physical perspectives. The components of malodorous gases are numerous and complex, often containing dozens or even hundreds of components, including both organic and inorganic. Some malodorous components contribute a lot to the dimensionless malodorous concentrations, but the real concentrations of the components may be very low, so the responses of a gas sensor are very small; some malodorous components contribute a little to the dimensionless malodorous concentrations, but the real concentrations may be very high, so the response of the gas sensor are very large; and vice versa. Considering the factors of sensitivity, selectivity, response speed, stability, commercialization, miniaturization, service life, cost and so on, the present disclosure selects MOS-type, EC-type and PID-type gas sensors to form a small-sized gas sensor array module. In order to avoid the wind, sun, and rain outside the monitoring areas, this disclosure proposes a centralized monitoring mode of multi-point malodorous gases with the key parts located indoors and develops an odor electronic nose instrument accordingly. In consideration of the complex composition of malodorous pollutants and the variable environment of the monitoring sites, this disclosure further proposes to establish the odor big data, and presents a new cascade machine learning model to realize online monitoring and prediction of various malodorous pollutants.

According to FIG. 1, the big data of malodorous gases include: (1) The off-line laboratory test data of the gas sensor array (I-1) of the odor electronic nose instrument for a large number of standard malodorous samples; including 5 kinds of standard malodorous liquids, i.e., β-phenylethanol, isovaleric acid, methylcyclopentanone, γ-undecanolide, β-methylindole; and 9 kinds of single standard malodorous compounds, i.e., $C_3H_9N$, $C_8H_8$, $H_2S$, $CH_4S$, $C_2H_6S$, $C_2H_6S_2$, $NH_3$, $CS_2$, $SO_2$, are prepared with different concentrations; in addition, also including the standard malodorous samples of mixed components prepared by a variety of the above compounds with different concentrations. (2) On-line detection data of a large number of malodorous pollutants by the gas sensor array (I-1). (3) Off-line olfactory data of a large number of malodorous pollutants in the laboratory for determining the dimensionless concentration values. (4) Off-line detection data of TVOCs and 9 kinds of malodorous components obtained by gas chromatographs, mass spectrometers and spectrophotometers for a large number of malodorous pollutants. (5) Complaint data of residents in the vicinities of malodorous pollution sources.

Figure 2:
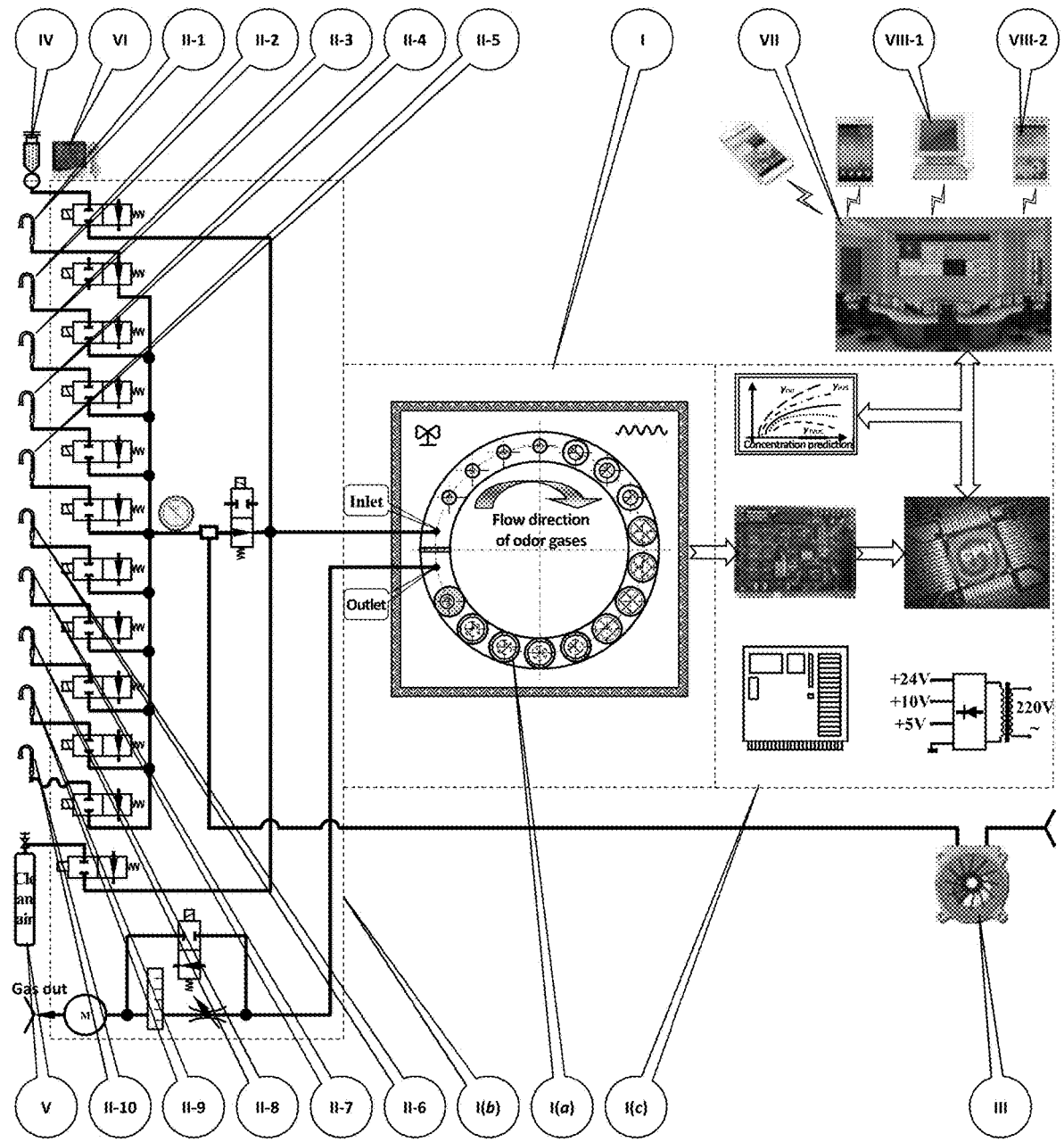
FIG. 2 illustrates a schematic diagram illustrating the working principle of the odor electronic nose instrument and multi-point centralized monitoring and analysis system for malodorous pollution sites according to the present disclosure named an online centralized monitoring and analysis system based on an electronic nose instrument for multi-point malodorous gases.

FIG. 2 is a schematic diagram illustrating the working principle of the odor electronic nose instrument and the centralized monitoring and analysis system for multiple malodorous pollution areas. The online centralized monitoring and analysis system based on an electronic nose Instrument for multiple malodorous pollution areas includes an odor electronic nose instrument (I), 10 sampling heads (II-1)~(II-10) for 10 outdoor monitoring points, an external vacuum pump (III), an ambient air purification device (IV), a clean air cylinder (V), an electronic hygrometer (VI), a central control room (VII), gas pipelines, as well as multiple stationary/mobile terminals (VIII), to realize the long-term online monitoring and the online estimation and prediction of important concentration control index values of malodorous gases for 10 points in some specified pollution areas. At this time, the gas paths and the electromagnetic valves are located at the working state by pumping the malodorous gas of the sampling head (II-1) from the first outdoor monitoring point to the odor electronic nose instrument (I), and the gas sensor array (I-1) thus produces its sensitive responses.

Figure 3:
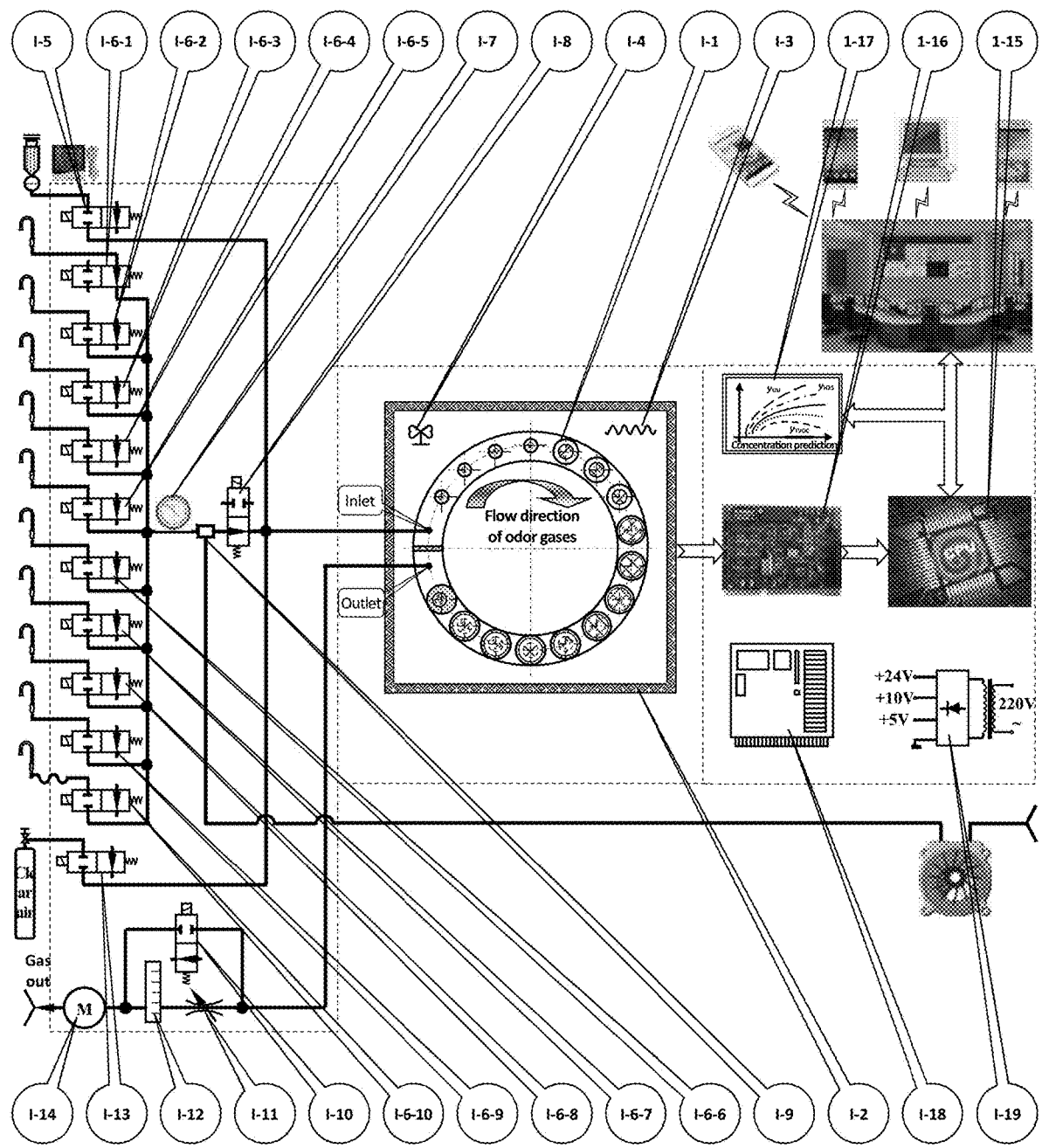
FIG. 3 illustrates a schematic diagram illustrating the working principle of the odor electronic nose instrument (in headspace sampling state) according to the present disclosure named an online centralized monitoring and analysis system based on an electronic nose instrument for multi-point malodorous gases.

FIG. 3 is a schematic diagram illustrating the working principle of the odor electronic nose instrument (I). The components of the instrument (I) include:

(a), The thermostatic gas sensor array working room (I(a)) is composed of a gas sensor array and an annular working chamber of the gas sensor array (I-1), a thermal insulation layer (I-2), a resistance heating wire (I-3) and a fan (I-4), located at the top right of the odor electronic nose instrument (I).

(b), The multi-point centralized malodorous auto-sampling system (I(b)) includes a first two-position two-port electromagnetic valves (I-5) to control the on-off of purified ambient air, 10 two-position two-port electromagnetic valves from the second two-position two-port electromagnetic valve (I-6-1) to the eleventh two-position two-port electromagnetic valve (I-6-10) to control the on-off of malodorous gases at 10 monitoring points, a vacuum pressure gauge (I-7) to show the working state of the external vacuum pump (III), the twelfth two-position two-port electromagnetic valve (I-8) to control when the malodorous gases flow into the annular working chamber of the gas sensor array (I-1), a gas buffer cavity (I-9), the thirteenth two-position two-port electromagnetic valve (I-10) to control the flow conversion between 6,500 ml/min of malodorous gases and 1,000 ml/min of clean air in the annular working chamber of the gas sensor array (I-1), a throttle valve (I-11), a flowmeter (I-12), a vacuum pressure gauge (I-7), and located at the lower right of the odor electronic nose instrument (I).

(c), The computer control and data analysis system (I(c)) includes a computer mainboard (I-15), a data acquisition card (I-16), a monitor (I-17), a drive and control circuit module (I-18), a precision linear and switching power module (I-19), a hard disk, a network card, a video card, located on the left side of the odor electronic nose instrument (I).

Figure 4:
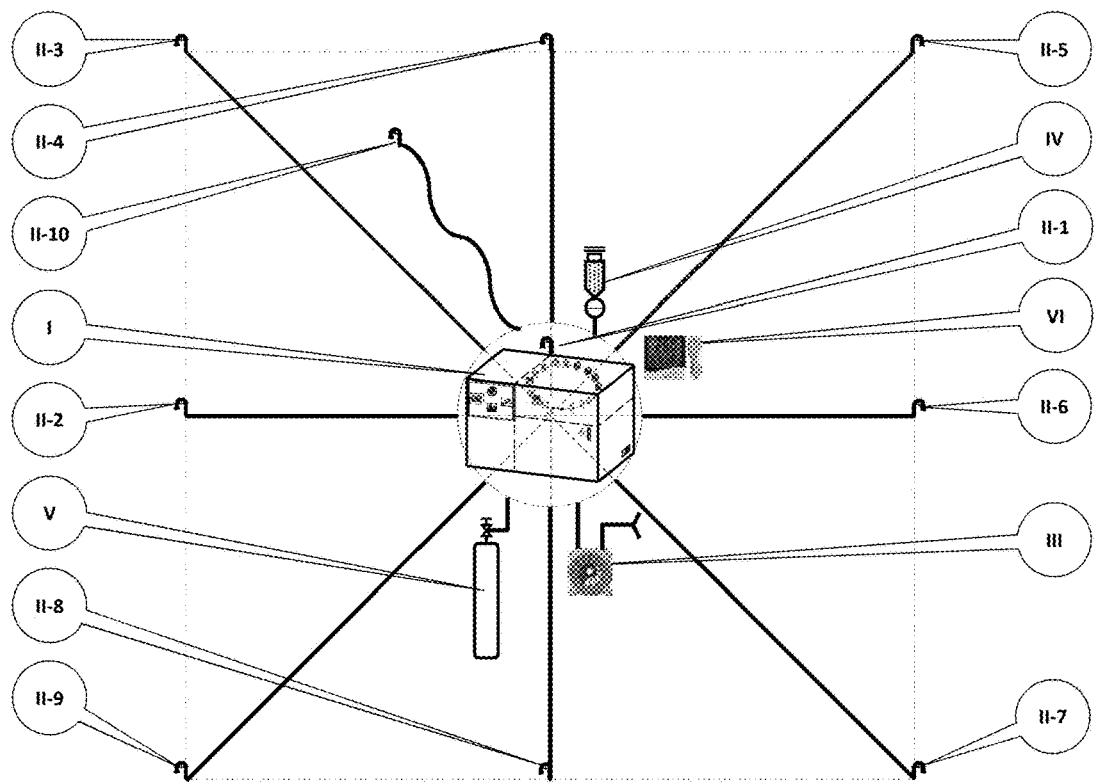
FIG. 4*a* illustrates a schematic diagram illustrating the mutual position relationship of the odor electronic nose instrument and multiple monitoring points in an area with road access according to the present disclosure named an online centralized monitoring and analysis system based on an electronic nose instrument for multi-point malodorous gases.
FIG. 4*b* illustrates a schematic diagram illustrating the mutual position relationship of the odor electronic nose instrument and multiple monitoring points in an area without road access according to the present disclosure named an online centralized monitoring and analysis system based on an electronic nose instrument for multi-point malodorous gases.
Figure 4:
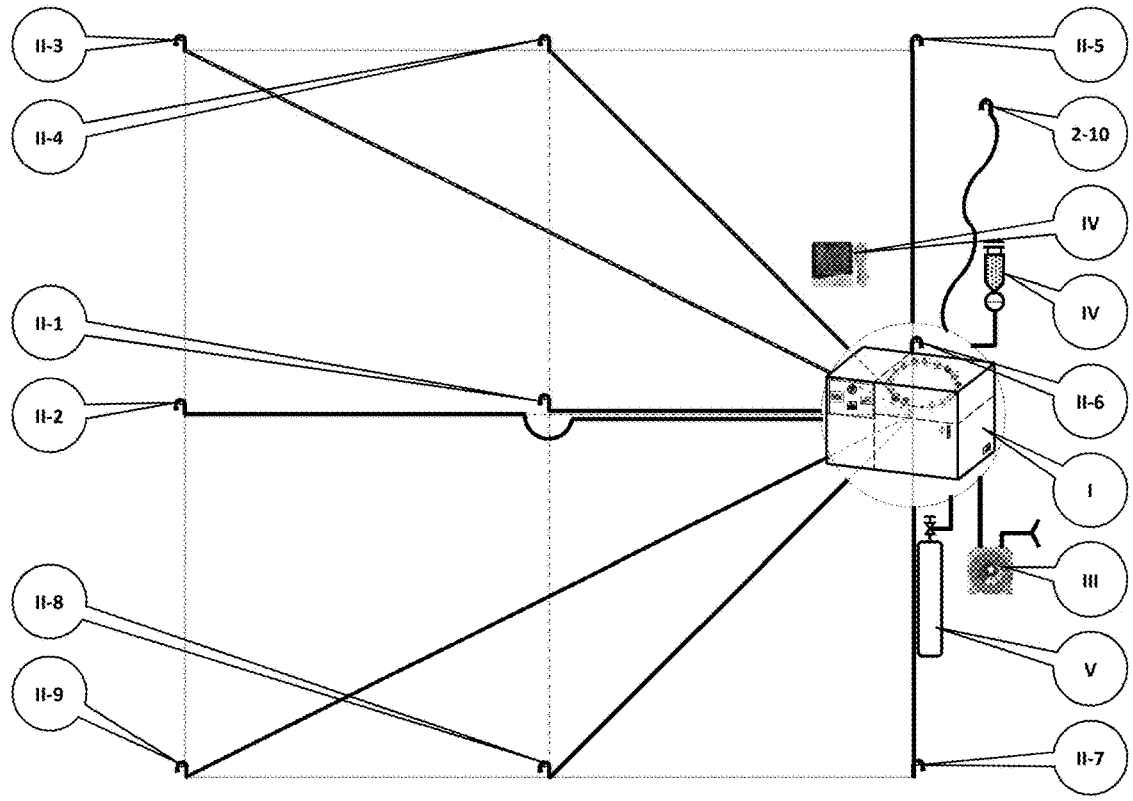

FIG. 4 is a schematic diagram illustrating the mutual positions of the odor electronic nose instrument (I) and 10 sampling heads (II-1)~(II-10) located at 10 monitoring points. (a) An area with road access; and (b) an area without road access. For the areas with access paths shown in FIG. 4(a), such as a chemical industry park or a residential area, the odor electronic nose instrument (I) ought to be arranged within a room in the center of the monitoring area; and for the areas without access roads shown in FIG. 4(b), the odor electronic nose instrument (I) ought to be arranged within a room at the boundary of the monitoring area. The position determination of the odor electronic nose instrument (I) is based on the rule of the shortest straight-line distance between it and each monitoring point. The external vacuum pump (III), the ambient air purification device (IV), the clean air cylinder (V) and the electronic hygrometer (VI) are arranged near the odor electronic nose instrument (I).

Suppose that the maximum monitoring area is 2 km*2 km=4 km² and the inner diameter of stainless steel pipe connecting odor electronic nose instrument (I) and each monitoring point is d=ϕ10 mm. let us consider the most disadvantageous situation: The longest gas pipeline appears in the area without road access as shown in FIG. 4(b), and the maximum straight-line length is $$l_{max} = \sqrt{2^2+1} = 2.24 \text{ km.}$$

Let us still assume that the maximum flow rate of the external vacuum pump (III) is Q=280 L/min and the maximum vacuum pressure is P=−100 mbar, the flow speed of the gas is v=4Q/(πd²)=59.42 m/s=3.57 km/min, and the malodorous gas is drawn from the farthest sampling point (II-3) or (II-9) to the odor electronic nose instrument (I) only needs $t_{max}=l_{max}/v=37.65$ s. It is noted that the maximum volume of the pipeline is about $U_{max}=I_{max}*\pi d^2/4=176L$, when $I_{max}=2.24$ km and d=ϕ10 mm, which is smaller than the maximum gas volume that can be drawn by the external vacuum pump (III) for 1 min, Q=250-280 L. Considering the leakage factor, it means that the time duration for the tested gas at a certain monitoring point to be pumped to the odor electronic nose instrument (I) is only about 1 min. In such a short time, there is no chance for the odor to undergo deterioration or adsorption effect.

The most industrial parks, waste and sewage treatment zones, breeding farms, adjacent residential areas and other pollution areas to be monitored are within the area of 1 km². Assuming that the maximum monitoring area is 1 km*1 km=1 km², and the gas pipeline connecting the odor the odor electronic nose instrument (I) and each monitoring point is arranged around the boundary, and still considering the disadvantageous situation that the longest gas pipeline is $I_{max}=0.5+1+0.5=2$ km, the external vacuum pump (III) can draw the gas from the monitoring point into the odor electronic nose instrument (I) within 1 min. In this disclosure, the odor electronic nose instrument and the multi-point centralized monitoring and analysis system for the malodorous pollution areas are particularly suitable for the places such as production workshops, sewage pools, breeding farms, etc., and can realize the online monitoring and analysis of some specific areas as large as several km², as small as a production workshop or a building, or even a point.

Figure 5:
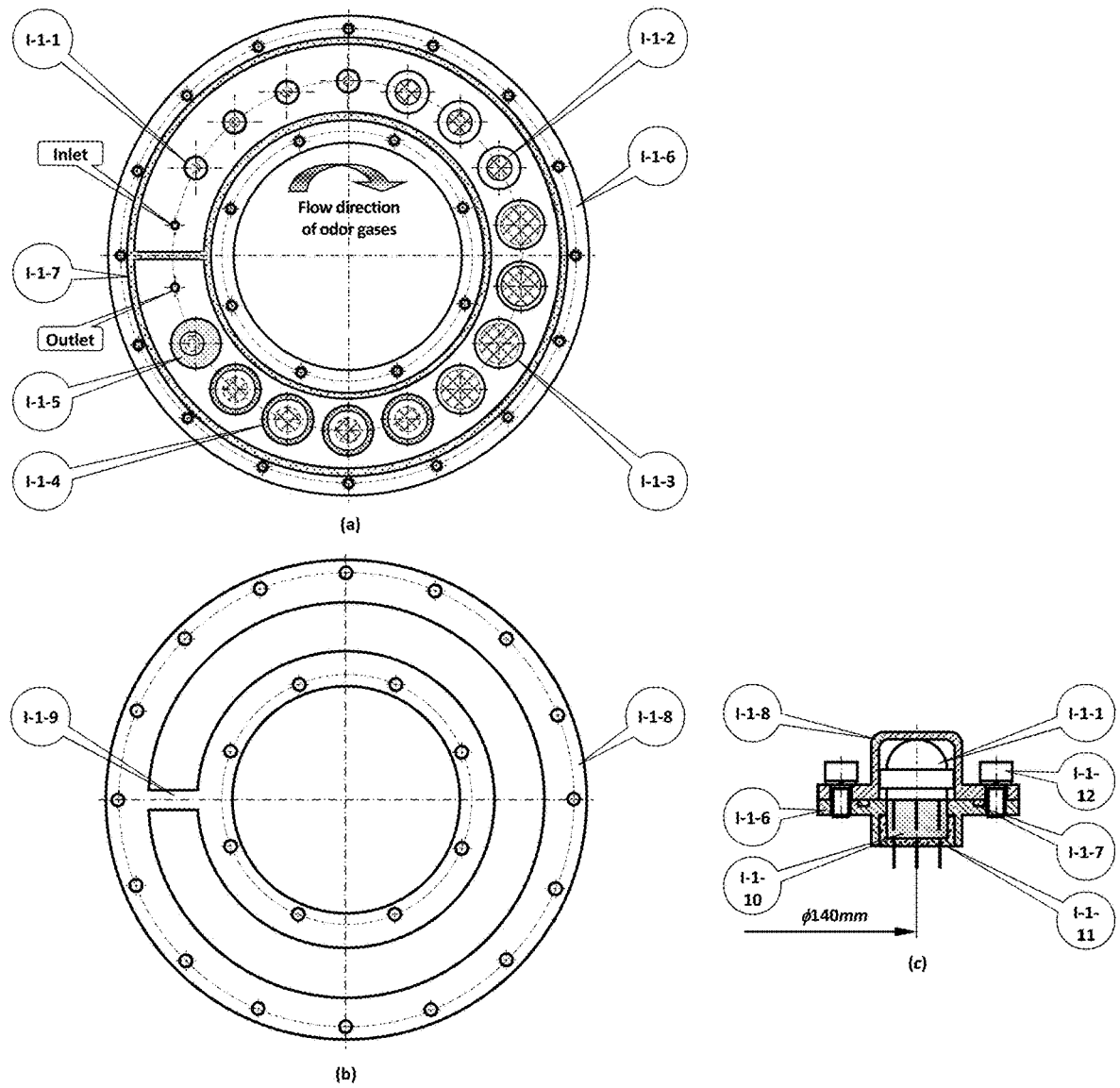
FIG. 5*a* illustrates a schematic diagram illustrating composition units of a gas sensor array according to the present disclosure named an online centralized monitoring and analysis system based on an electronic nose instrument for multi-point malodorous gases.
FIG. 5*b* illustrates a schematic diagram illustrating an annular working chamber cover according to the present disclosure named an online centralized monitoring and analysis system based on an electronic nose instrument for multi-point malodorous gases.
FIG. 5*c* illustrates a schematic diagram illustrating a sectional drawing of an annular working chamber according to the present disclosure named an online centralized monitoring and analysis system based on an electronic nose instrument for multi-point malodorous gases.

FIG. 5 is a schematic diagram illustrating the arrangement of the gas sensor array (I-1) and the annular working chamber. FIG. 5(a) shows such a specific example: The gas sensor array consists of 16 sensitive with three types, including 11 MOS-type, i.e., four TGS2000 series (I-1-1), three TGS800 series with plastic shell (I-1-2), four TGS800 series (I-1-3) with stainless steel shell; four EC-type (I-1-4) and one PID-type (I-1-5). The MOS-type gas sensors have high sensitivity, long life and are sensitive to both organic and inorganic components; the EC-type gas sensors have good selectivity and are mainly used to detect the inorganic gases; and the PID gas sensor is sensitive to the VOCs between n-hexane and n-cetane. The cascade machine learning model determines the concentrations of $H_2S$, $NH_3$, $SO_2$, $CS_2$ and other inorganic components depending upon the responses of eleven MOS-type and four EC-type gas sensors; estimates the concentration values of TVOCs and such organic components as $C_3H_9N$, $C_8H_8$, $CH_4S$, $C_2H_6S$, $C_2H_6S_2$ depending upon the responses of eleven MOS-type gas sensors and one PID-type, and quantizes the dimensionless concentration OU values depending upon the responses of all the 16 gas sensors.

According to FIGS. 5(a), 5(b) and 5(c), the working chamber of gas sensor array (I-1) is composed of stainless steel base (I-1-6), sealing ring (I-1-7), stainless steel cover (I-1-8), partition (I-1-9), gas sensor socket (I-1-10), sealing material (I-1-11) and screw (I-1-12), forming a sealed annular chamber. During the headspace sampling, the malodorous gas is inhaled from the gas inlet, then passes through four TGS2000-series (I-1-1), three TGS800-series (I-1-2) with plastic shell, four TGS800-series (I-1-3) with stainless steel shell, four EC-type (I-1-4) and one PID-type gas sensor (I-1-5) around the working chamber, in order, and finally flows out from the air outlet. As a result, the gas sensor array generates the sensitive responses.

Figure 6:
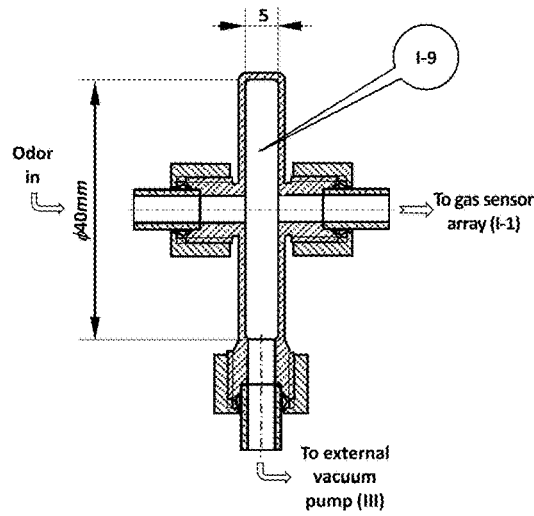
FIG. 6 illustrates a schematic diagram illustrating an odor buffer cavity according to the present disclosure named an online centralized monitoring and analysis system based on an electronic nose instrument for multi-point malodorous gases.

FIG. 6 is a schematic diagram illustrating the gas buffer cavity (I-9). The buffer cavity is located within the odor electronic nose instrument (I), with an inner diameter of ϕ40 mm and a clear depth of 5-10 mm. Because the ratio between the inner diameter of the buffer cavity and the inner diameter of the gas pipelines connecting the odor electronic nose instrument (I) and 10 sampling heads (II-1)~(II-10) located at 10 monitoring points is 4:1, the gas flow speed in this buffer cavity drops 16 times than in the pipelines, and the internal miniature vacuum pump (I-14) can draw enough malodorous gas from here.

Figure 7:
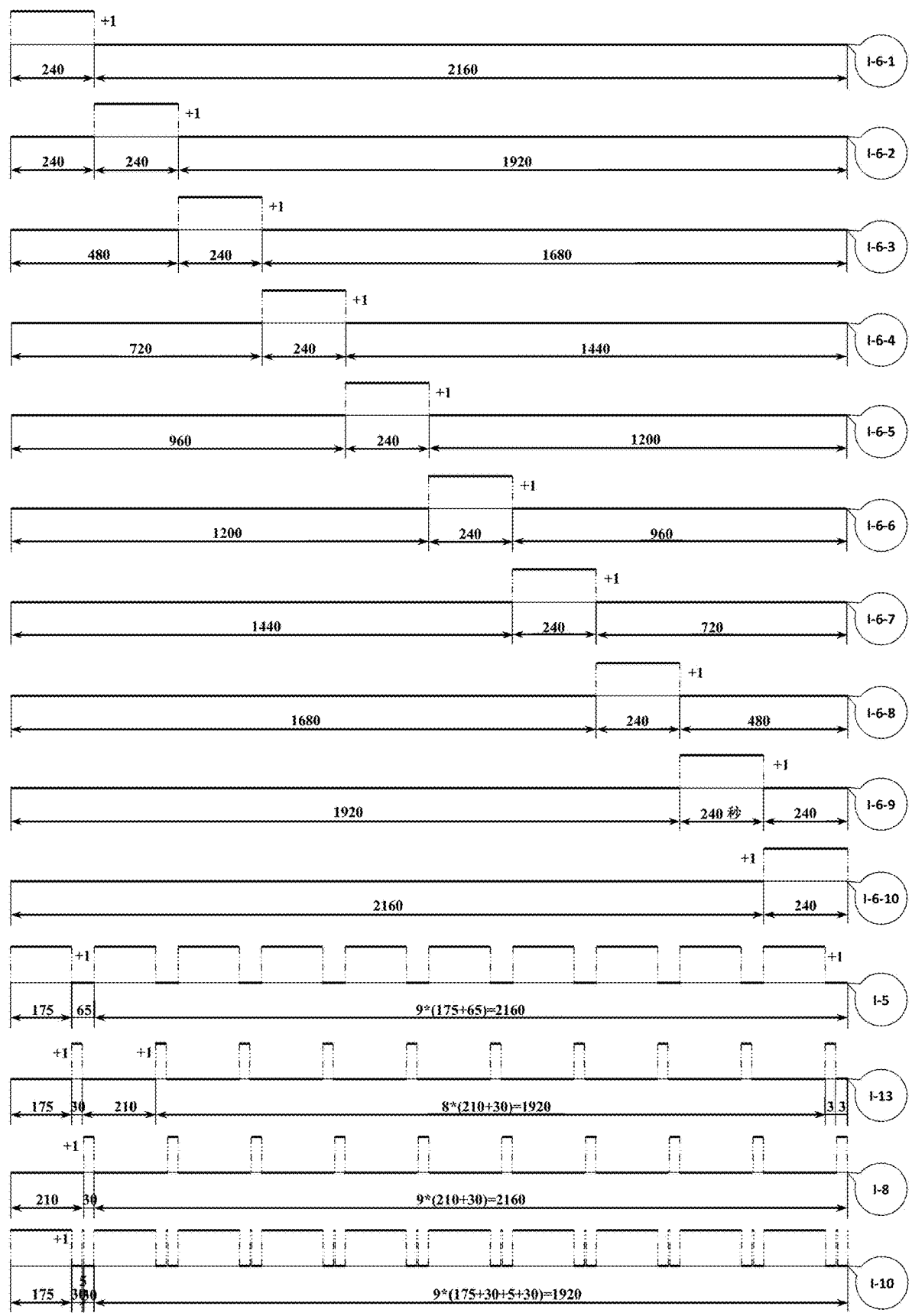
FIG. 7 illustrates an on-off change diagram of 14 two-position two-port electromagnetic valves (in seconds) with a single gas sampling period of $T_0=240$ s and a cyclic gas sampling period $T=10T_0$ according to the present disclosure named an online centralized monitoring and analysis system based on an electronic nose instrument for multi-point malodorous gases.

FIG. 7 shows the on-off changes and mutual relationship of 14 two-position two-port electromagnetic valves in the centralized automatic sampling system of multi-point malodorous gases when the single sampling period is $T_0$ and the cycle period is $T=10 T_0$. In the cycle sampling period T, the 10 two-position two-port electromagnetic valves from the second two-position two-port electromagnetic valve (I-6-1) to the eleventh two-position two-port electromagnetic valve (I-6-10) that control the on-off states of malodorous gases at 10 monitoring points are only on and off once. At any time in any single gas sampling period $T_0$, among 10 two-position two-port electromagnetic valves, only one is on, and the other nine are off.

In the cyclic sampling period T, the first two-position two-port electromagnetic valve (I-5) that controls the on-off of purified ambient air, the twelfth two-position two-port electromagnetic valve (I-8) that controls the malodorous gas flowing into the annular working chamber of gas sensor array and the fourteenth two-position two-port electromagnetic valve (I-13) that controls the on-off of clean air are on-off for 10 times, and the thirteenth two-position two-port electromagnetic valve (I-10) that controls the flow conversion is on-off for 20 times.

Referring now to FIG. 7. Taking as an example the first single sampling period $T_0$=240 seconds within the cyclic sampling period $T=10T_0$, there are the several following situations:

(a), The whole single sampling period of $T_0$=240s. Among the 10 two-position two-port electromagnetic valves, the second two-position two-port electromagnetic valve (I-6-1) is always on, and the other nine two-position two-port electromagnetic valves are disconnected. Under the suction action of the external vacuum pump (III), the malodorous gas sequentially flows through the sampling head (II-1) located at the first monitoring point, pipelines, the second two-position two-port electromagnetic valve (I-6-1), the gas buffer cavity (I-9) and the external vacuum pump (III) with a flow rate of 250-280 l/min, and is finally discharged to outdoor.

(b), The 0-175 s segment in the single sampling period $T_0$. Although the external vacuum pump (III) draws the measured malodorous gas of the sampling head (II-1) from the first monitoring point to the odor electronic nose instrument (I), because the twelfth two-position two-port electromagnetic valve (I-8) is disconnected, the malodorous gas at this time does not flow through the annular working chamber of the gas sensor array (I-1) of the gas sensor array, but is directly discharged from the external vacuum pump (III) to outdoor. The period of 175s can be further divided into two sub-stages: (b1), the first 155 s for the preliminary recovery stage of the gas sensor array; and (b2), the last 20 s for the flushing stage of the gas sensor array. In the two time sub-stages, the fourteenth two-position two-port electromagnetic valve (I-13) is disconnected, the first two-position two-port electromagnetic valve (I-5) and the thirteenth two-position two-port electromagnetic valve (I-10) are on, and under the suction action of the internal miniature vacuum pump (I-14), the purified ambient air by the ambient air purification device (IV) sequentially flows through the first two-position two-port electromagnetic valve (I-5), the gas pipelines, the annular working chamber of the gas sensor array (I-1), the thirteenth two-position two-port electromagnetic valve (I-10) and the internal miniature vacuum pump (I-14) with a flow rate of 6,500 ml/min, and then is discharged to outdoor.

(c), The 176-205 s in the single sampling period $T_0$=240 seconds. The first two-position two-port electromagnetic valve (I-5), the twelfth two-position two-port electromagnetic valve (I-8) and the thirteenth two-position two-port electromagnetic valve (I-10) are disconnected, and the fourteenth two-position two-port electromagnetic valve (I-13) is on. The clean air in the clean air cylinder (V) sequentially flows by the own pressure through the fourteenth two-position two-port electromagnetic valve (I-13), gas pipelines, the annular working chamber of the gas sensor array (I-1), the flowmeter (I-12) and the internal miniature vacuum pump (I-14) with a flow rate of 1,000 ml/min, and then is discharged to outdoor.

(d), The 111-240 s in the single sampling period $T_0$=240 seconds. The first two-position two-port electromagnetic valve (I-5), the twelfth two-position two-port electromagnetic valve (I-8) and the thirteenth two-position two-port electromagnetic valve (I-10) are disconnected, and the twelfth two-position two-port electromagnetic valve (I-8) is on. Under the suction effect of the internal miniature vacuum pump (I-14), the malodorous gas sequentially flows through the fourteenth two-position two-port electromagnetic valve (I-13), gas pipelines, the annular working chamber of the gas sensor array (I-1), the flowmeter (I-12) and the internal miniature vacuum pump (I-14) with a flow rate of 1,000 ml/min, and then is discharged to outdoor.

Figure 8:
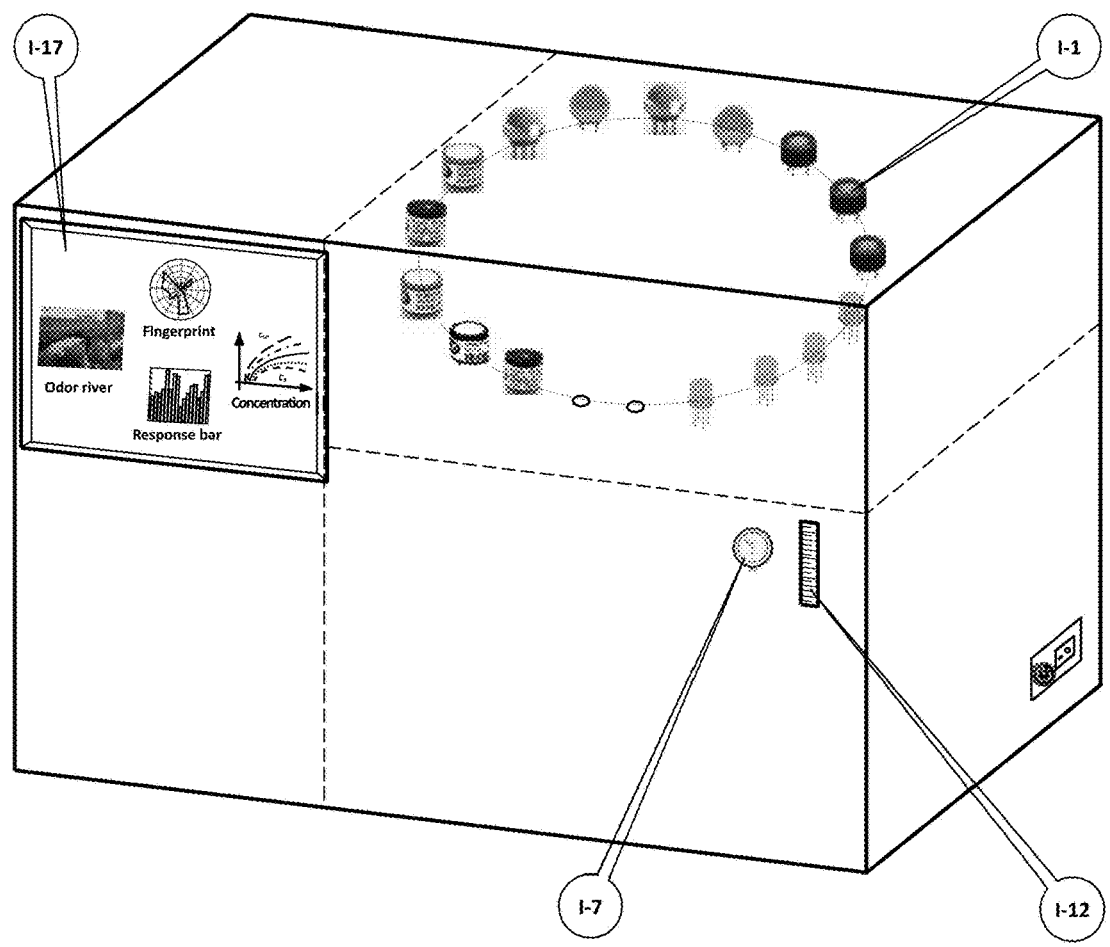
FIG. 8 illustrates a schematic diagram illustrating the three-dimensional appearance of the odor electronic nose instrument according to the present disclosure named an online centralized monitoring and analysis system based on an electronic nose instrument for multi-point malodorous gases.

FIG. 8 is a schematic diagram illustrating the three-dimensional appearance of the odor electronic nose instrument (I). The gas sensor array (I-1) is located in the upper right part of the odor electronic nose instrument (I). The monitor (I-17), the vacuum pressure gauge (I-7) and the flowmeter (I-12) can be seen from the front view.

Figure 9:
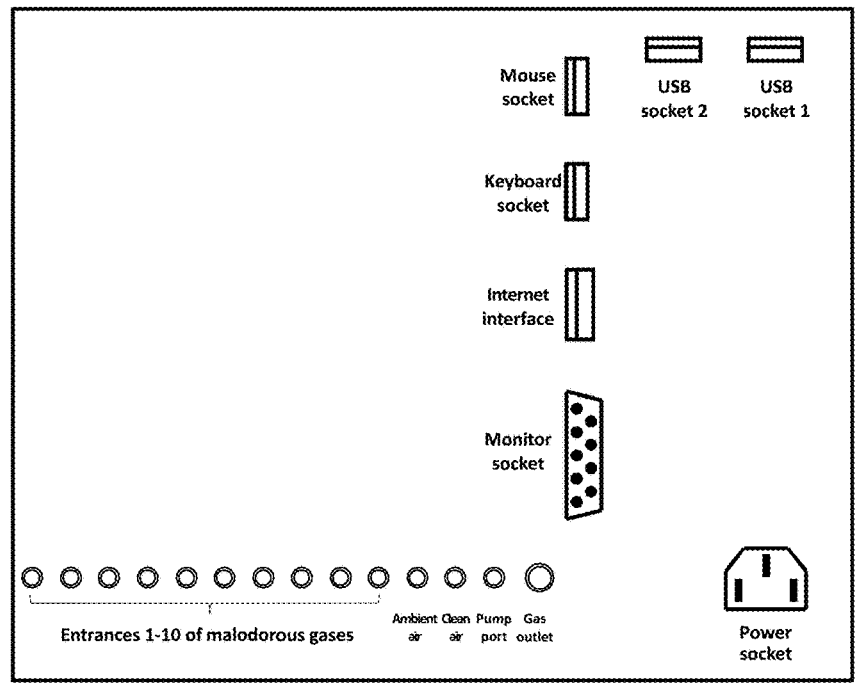
FIG. 9 illustrates a schematic diagram illustrating a back of the odor electronic nose instrument according to the present disclosure named an online centralized monitoring and analysis system based on an electronic nose instrument for multi-point malodorous gases.

FIG. 9 is a schematic diagram illustrating the back of the odor electronic nose instrument (I). The odor electronic nose instrument (I) is set with an interface for the external monitor, 2 USB interfaces, a mouse interface, a keyboard interface, an Internet interface, a clean and a purified air inlet, 10 inlets for the malodorous gases of 10 monitoring points, an outlet for the external vacuum pump (III) and an exhaust gas outlet.

In the 45 s response data recorded in a single sampling period $T_0$, the difference between the steady-state maximum value $U_{imax}(t)$ and the minimum value $U_{imin}(t)$ of the response curve of a single gas sensor i is extracted as the characteristic component $x_i(t)=U_{imax}(t)-U_{imin}(t)$. Therefore, the gas sensor array generates a 16-dimensional response vector $x(t)=(x_1(t), \ldots, x_i(t), \ldots, x_{16}(t))^T \in R^{16}$. Within 10 seconds after the end of data recording, i.e., 10 seconds after the ambient air flushing stage, the cascade machine learning model of the computer control and data analysis system (I(c)) predicts 10+1 concentration control index values of malodorous pollutants based on the 16-dimensional response vector x(t).

Figure 10:
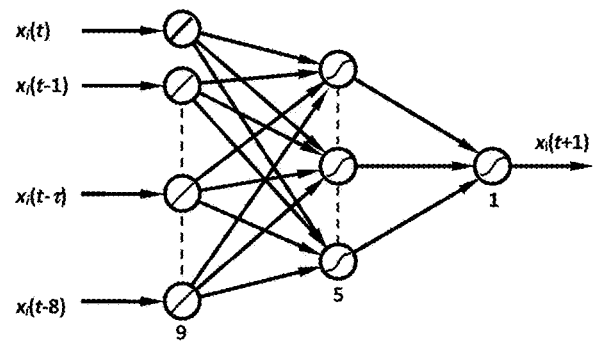
FIG. 10 illustrates a schematic diagram illustrating a convolutional neural network $CNN_{i1}$ to predict the response $x_i(t+1)$ of a gas sensor i at the time point of t+1 (i.e. the $40^{th}$ minute in the future) according to the present disclosure named an online centralized monitoring and analysis system based on an electronic nose instrument for multi-point malodorous gases.

According to the "divide-and-conquer" strategy, the first level of the cascade machine learning model, namely, the convolution neural network layer, uses multiple single-output single-hidden-layer convolution neural networks to predict the response of each gas sensor. FIG. 10 is the schematic diagram illustrating the structure of the convolutional neural network $CNN_{i1}$ for predicting the response $x_i(t+1)$ of the gas sensor i at the time point of t+1 (say the $40^{th}$ minute in the near future). Table 2(a) shows the time-series response of the training set $X_{i1} \in R^{10 \times 9}$ of the $CNN_{i1}$, with ten 9-dimensional samples in total. The time-series span of the training set $X_{i1}$ is [t-18, t-1]. When $T_0$=240 s and $T=10T_0$, it is equivalent to the $CNN_{i1}$ to learning the responses of the gas sensor i what have happened from the 12 hours ago to the current time. According to Table 2(a), a learning sample of $CNN_{i1}$ is equivalent to a time-series response of the gas sensor i with the time length $\Delta t=9$. Table 2(b) shows such a response sample $x_1=(x_i(t-8), \ldots, x_i(t))^T \in R^9$.

TABLE 2(a)

The time-series training set $X_{i1}$ of the convolutional neural network $CNN_{i1}$.

| _____ Input node _____ | | | | | | | | | Desired | |
|---|---|---|---|---|---|---|---|---|---|---|
| 1 | 2 | 3 | 4 | 5 | 6 | 7 | 8 | 9 | output | #Sample |
| $x_i(t-9)$ | $x_i(t-8)$ | $x_i(t-7)$ | $x_i(t-6)$ | $x_i(t-5)$ | $x_i(t-4)$ | $x_i(t-3)$ | $x_i(t-2)$ | $x_i(t-1)$ | $x_i(t)$ | 1 |
| $x_i(t-10)$ | $x_i(t-9)$ | $x_i(t-8)$ | $x_i(t-7)$ | $x_i(t-6)$ | $x_i(t-5)$ | $x_i(t-4)$ | $x_i(t-3)$ | $x_i(t-2)$ | $x_i(t-1)$ | 2 |
| | | | | . . . | | | | | | . . . |
| $x_i(t-17)$ | $x_i(t-16)$ | $x_i(t-15)$ | $x_i(t-14)$ | $x_i(t-13)$ | $x_i(t-12)$ | $x_i(t-11)$ | $x_i(t-10)$ | $x_i(t-9)$ | $x_i(t-8)$ | 9 |
| $x_i(t-18)$ | $x_i(t-17)$ | $x_i(t-16)$ | $x_i(t-15)$ | $x_i(t-14)$ | $x_i(t-13)$ | $x_i(t-12)$ | $x_i(t-11)$ | $x_i(t-10)$ | $x_i(t-9)$ | 10 |

TABLE 2(b)

The time-series response $x_i(t)$ of gas sensor array learned by the $CNN_{i1}$ to predict $x_i(t+1)$ at the time point of $t+1$

| _____ Input node _____ | | | | | | | | | Predicted | |
|---|---|---|---|---|---|---|---|---|---|---|
| 1 | 2 | 3 | 4 | 5 | 6 | 7 | 8 | 9 | output | #Sample |
| $x_i(t-8)$ | $x_i(t-7)$ | $x_i(t-6)$ | $x_i(t-5)$ | $x_i(t-4)$ | $x_i(t-3)$ | $x_i(t-2)$ | $x_i(t-1)$ | $x_i(t)$ | $x_i(t+1)$ | 1 |

The convolutional neural network $CNN_{i1}$ learns the time-series responses of the gas sensor i at 18 times that have occurred before the time t. If the delay length $\Delta t=9$, then the number of input nodes is set to be $m_i=9$. The number of hidden nodes is set to be $h_i=5$, and the number of output nodes is set to be $n_i=1$. The convolutional neural network $CNN_{i1}$ online learns the preprocessed time-series responses of the gas sensor i—the data set $X_{i1}$, as shown in Table 2(a). The hidden and output activation functions of the $CNN_{i1}$ are the modified Sigmoid function $f(\varphi)=3/(1+\exp(-\varphi/3))$, and the error back-propagation algorithm is used for learning. The learning factor is $\eta_{i1}=(5/N_{i1})=0.5$, and the maximum number of iterations is 10,000. The input and output components in Tables 2(a) and 2(b) are scaled to the range of [0, 3].

the convolutional neural network $CNN_{i1}$ completes online learning within 10 seconds after the ambient air flushing phase of the gas sensor array, and thus predicts the response $x_i(t+1)$ of the gas sensor i at the time point of t+1 according to the time-series response sample $x_i(t)=(x_i(t-8), \ldots, x_i(t))^T$ given in Table 2(b).

The present disclosure uses the convolution neural networks $CNN_{i2}$ and $CNN_{i3}$ to predict the responses $x_i(t+2)$ and $x_i(t+3)$ of the gas sensor i at the time point of t+2 (for example, the $80^{th}$ minute in the future) and the time point of t+3 (for example, the $120^{th}$ minute in the future), respectively. The structure and learning parameters of $CNN_{i2}$ and $CNN_{i3}$ are the same as those of $CNN_{i1}$. Tables 3 and 4 show the time-series response training sets $X_{i2} \in R^{10 \times 9}$ and $X_{i3} \in R^{10 \times 9}$ for the two convolutional neural networks. The $CNN_{i2}$ and $CNN_{i3}$ still use the same time-series response samples $x_i(t)$ as the $CNN_{i1}$ shown in Table 2(b) to predict the responses $x_i(t+2)$ and $x_i(t+3)$ of the gas sensors i at the time points of t+2 and t+3, respectively. Compared with the time span of [t–18, t–1] in the dataset $X_{i1}$, the time spans of $X_{i2}$ and $X_{i3}$ are [t–19, t–2] and [t–20, t–3], respectively, which are a little far away from the current time t. Therefore, the reliability of the predicted values of the $CNN_{i2}$ and $CNN_{i3}$ is relatively low, compared with that of the $CNN_{i1}$.

TABLE 3

The time-series training set $X_{i2}$ of the convolutional neural network $CNN_{i2}$.

| _____ Input node _____ | | | | | | | | | Desired | |
|---|---|---|---|---|---|---|---|---|---|---|
| 1 | 2 | 3 | 4 | 5 | 6 | 7 | 8 | 9 | output | #Sample |
| $x_i(t-10)$ | $x_i(t-9)$ | $x_i(t-8)$ | $x_i(t-7)$ | $x_i(t-6)$ | $x_i(t-5)$ | $x_i(t-4)$ | $x_i(t-3)$ | $x_i(t-2)$ | $x_i(t)$ | 1 |
| $x_i(t-11)$ | $x_i(t-10)$ | $x_i(t-9)$ | $x_i(t-8)$ | $x_i(t-7)$ | $x_i(t-6)$ | $x_i(t-5)$ | $x_i(t-4)$ | $x_i(t-3)$ | $x_i(t-1)$ | 2 |
| | | | | . . . | | | | | | . . . |
| $x_i(t-18)$ | $x_i(t-17)$ | $x_i(t-16)$ | $x_i(t-15)$ | $x_i(t-14)$ | $x_i(t-13)$ | $x_i(t-12)$ | $x_i(t-11)$ | $x_i(t-10)$ | $x_i(t-8)$ | 9 |
| $x_i(t-19)$ | $x_i(t-18)$ | $x_i(t-17)$ | $x_i(t-16)$ | $x_i(t-15)$ | $x_i(t-14)$ | $x_i(t-13)$ | $x_i(t-12)$ | $x_i(t-11)$ | $x_i(t-9)$ | 10 |

TABLE 4

The time-series training set $X_{i3}$ of the convolutional neural network $CNN_{i3}$.

| _____ Input node _____ | | | | | | | | | Desired | |
|---|---|---|---|---|---|---|---|---|---|---|
| 1 | 2 | 3 | 4 | 5 | 6 | 7 | 8 | 9 | output | #Sample |
| $x_i(t-11)$ | $x_i(t-10)$ | $x_i(t-9)$ | $x_i(t-8)$ | $x_i(t-7)$ | $x_i(t-6)$ | $x_i(t-5)$ | $x_i(t-4)$ | $x_i(t-3)$ | $x_i(t)$ | 1 |
| $x_i(t-12)$ | $x_i(t-11)$ | $x_i(t-10)$ | $x_i(t-9)$ | $x_i(t-8)$ | $x_i(t-7)$ | $x_i(t-6)$ | $x_i(t-5)$ | $x_i(t-4)$ | $x_i(t-1)$ | 2 |
| | | | | . . . | | | | | | . . . |

TABLE 4-continued

The time-series training set $X_{i3}$ of the convolutional neural network $CNN_{i3}$.

| Input node | | | | | | | | | Desired | |
|---|---|---|---|---|---|---|---|---|---|---|
| 1 | 2 | 3 | 4 | 5 | 6 | 7 | 8 | 9 | output | #Sample |
| $x_i(t-19)$ | $x_i(t-18)$ | $x_i(t-17)$ | $x_i(t-16)$ | $x_i(t-15)$ | $x_i(t-14)$ | $x_i(t-13)$ | $x_i(t-12)$ | $x_i(t-11)$ | $x_i(t-8)$ | 9 |
| $x_i(t-20)$ | $x_i(t-19)$ | $x_i(t-18)$ | $x_i(t-17)$ | $x_i(t-16)$ | $x_i(t-15)$ | $x_i(t-14)$ | $x_i(t-13)$ | $x_i(t-12)$ | $x_i(t-9)$ | 10 |

The three networks, $CNN_{i1}$, $CNN_{i2}$ and $CNN_{i3}$, all completed their online learnings and predictions within 10 seconds after the ambient air flushing phase of the gas sensor array. Therefore, 3*16 convolution neural networks are adopted in the present disclosure to predict the responses at the time points of t+1, t+2 and t+3 for all 16 response curves of the gas sensor array. If only the response at the time point of t+1 is predicted, only 16 single-output convolution neural networks are needed.

According to the "divide-and-conquer" strategy, the present disclosure decomposes the overall prediction problem of multiple concentration values of malodorous gas into multiple individual concentration value prediction problems, and uses the second level of the cascade machine learning model, i.e. multiple single-output depth neural networks, to predict multiple individual concentration values one by one, thereby effectively reducing the complexity of machine learning models and algorithms. The number of the single-output DNNs are equal to the number of concentration control indicators of malodorous gases to be predicted, namely they are in one-to-one correspondence. For example, 10+1 single-output DNNs are needed to predict the dimensionless concentration OU value, the concentration values of 9 specified compounds including $NH_3$, $H_2S$, $CS_2$, $C_3H_9N$, $CH_4S$, $C_2H_6S$, $C_2H_6S_2$, $C_8H_8$, $SO_2$, as well as the TVOC concentration value, present in malodorous pollutants. A single-output DNN learns the big data of malodorous gases. The input values are the detection data of the gas sensor array as well as the temperature and humidity data on the site of the odor electronic nose instrument, and the target output is the off-line measurement values of odor olfactory identification, the conventional instruments including gas chromatography, mass spectrometry, and others, as well as the data of residents' complaints. Some samples in the big data of malodorous gases that only have the responses of the gas sensor array but without the off-line measurement values such as dimensionless olfactory discrimination, gas chromatography, mass spectrometry and residents' complaint data, will not participate in the study.

Figure 11:
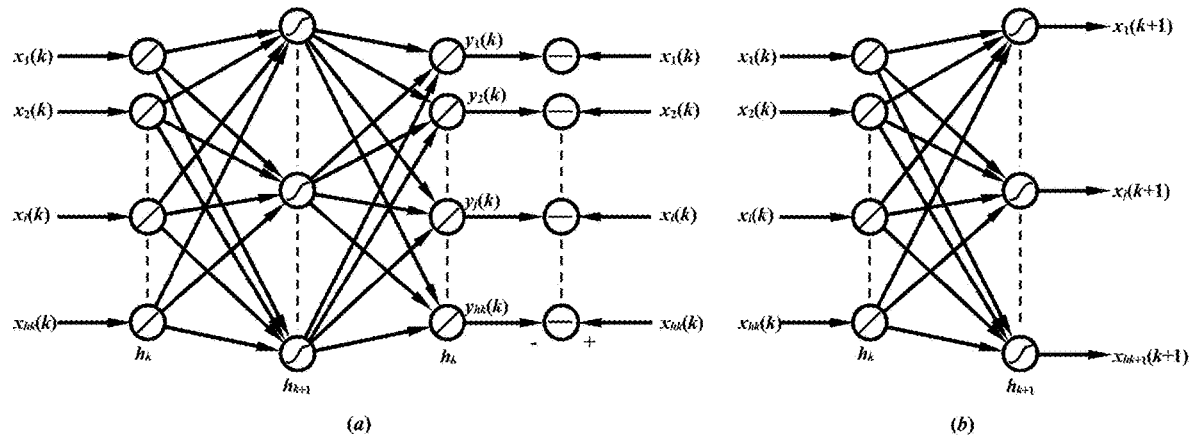
FIG. 11a illustrates a learning process diagram of a $k^{th}$ layer in a deep neural network $DNN_j$, where a structure and parameters of a single-hidden-layer peer-to-peer neural network, according to the present disclosure named an online centralized monitoring and analysis system based on an electronic nose instrument for multi-point malodorous gases.
FIG. 11b illustrates a learning process diagram of a $k^{th}$ layer in a deep neural network $DNN_j$, where a reserved structure after a learning of a peer-to-peer neural network, according to the present disclosure named an online centralized monitoring and analysis system based on an electronic nose instrument for multi-point malodorous gases.

A single-output $DNN_j$ has three hidden layers, and the hidden-layer and the output-layer nodes use the modified Sigmoid activation function $f(\varphi)=3/(1+\exp(\varphi/3))$; the response data of the gas sensor arrays and the target output components are respectively and proportionally transformed to the ranges of [0, 3]. The first and second hidden layers are the feature transformation (coding) layers. The structure and weight parameters are determined by the single-hidden-layer and peer-to-peer neural networks. FIG. 11 shows the learning process of a peer-to-peer neural network to determine the weights and thresholds of between the kth and the $(k+1)^{th}$ hidden layer in the $DNN_j$. FIG. 11(a) shows that the number of the output and the input nodes in a peer-to-peer neural network are equal, both of which are linear activation functions; the weights and thresholds of the hidden-to-output layer are directly equal to those of its input-to-hidden layer, and the target outputs are directly equal to their actual inputs. FIG. 11(b) shows that after the learning of the peer-to-peer neural network, the number of hidden nodes in the $(k+1)^{th}$ layer of $DNN_j$ is equal to the number of hidden nodes in the peer-to-peer neural network, and the weights and thresholds of between the $k^{th}$ and the $(k+1)^{th}$ layer are equal to those in the input-to-hidden layer of the peer-to-peer neural network. If the number of the learning samples of the $DNN_j$ is N, then the learning factor of the peer-to-peer neural network is $\eta=2/N$, and the maximum number of iterative steps is $\tau_{max}=10,000$. The third hidden layer of the $DNN_j$ is a nonlinear mapping layer, which is used to fit the $j^{th}$ concentration control index value of malodorous gases with the single output unit j.

Figure 12:
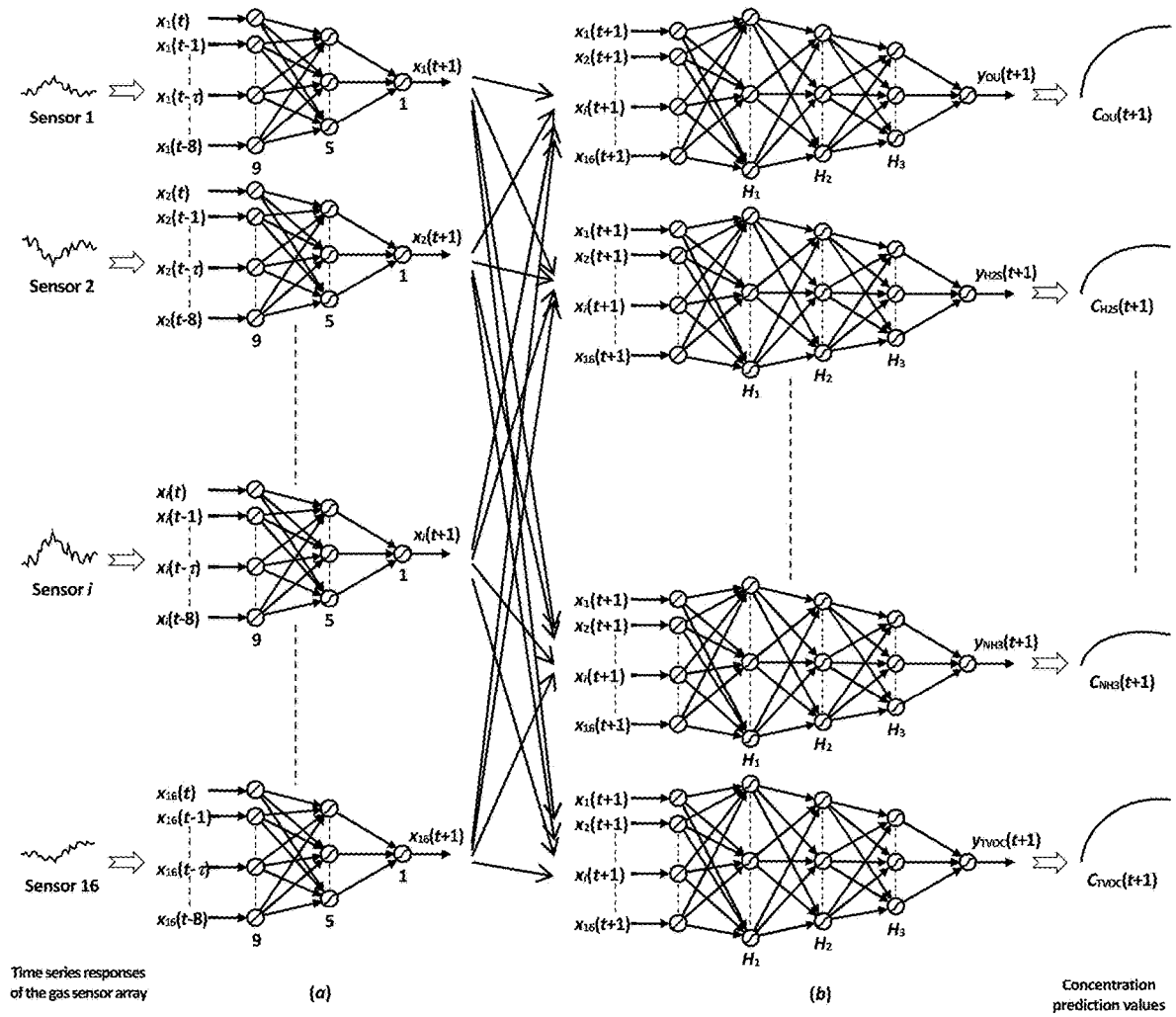
FIG. 12a illustrates a schematic diagram illustrating a concentrations of multiple malodorous pollutants at the time point of t+1 (say the $40^{th}$ minute in the future) with a first level of a cascade machine learning model, i.e. a convolution neural network layer, according to the present disclosure named an online centralized monitoring and analysis system based on an electronic nose instrument for multi-point malodorous gases.
FIG. 12b illustrates a schematic diagram illustrating a concentrations of multiple malodorous pollutants at the time point of t+1 (say the $40^{th}$ minute in the future) with a second level of a cascade machine learning model, i.e. the deep neural network (DNN) layer, according to the present disclosure named an online centralized monitoring and analysis system based on an electronic nose instrument for multi-point malodorous gases.

FIG. 12 is a schematic diagram illustrating the cascade machine learning model to predict the concentrations of various malodorous pollutants at the time point of t+1 (say the $40^{th}$ minute in the coming future). According to FIG. 12(a), the first level of the cascade machine learning model uses 16*3 groups of single-output single-hidden-layer convolution neural networks to learn the time-series responses generated by 16 gas sensors, and then to predict the responses of each gas sensor at the time points of t+1, t+2 and t+3, respectively according to the time-series response sample $x_i(t)=(x_i(t-8), \ldots, x_i(t))^T$. In the second level of the cascade machine learning model, 10+1 single-output three-hidden-layer depth neural network modules are used to predict the above 10+1 malodorous concentration control indicator values.

Assuming that the DNN predicts the concentration value $y_j(t+1)$ of a malodorous gas at the time point of t+1, it is based on the predicted response vector $(x_1(t+1), x_2(t+1), \ldots, x_{16}(t+1))^T$ by the previous 16 $CNN_{i1}$ (i=1, 2, ..., 16) and the current temperature and humidity values; the DNN forecasts $y_j(t+1)$ based on the predicted response vector $(x_1(t+2), x_2(t+2), \ldots, x_{16}(t+2))^T$ by the previous 16 $CNN_{i2}$ and current temperature and humidity values, and so on.

If the actual input is the current response vector of the gas sensor array $(x_1(t), x_2(t), \ldots, x_{16}(t))^T$, and the temperature and the humidity values at the current time t are added if necessary, the actual output of $DNN_j$ is the estimating value of the current concentration $y_j(t)$ of the malodorous component j.

What is claimed is:

1. An online centralized monitoring and analysis system based on an electronic nose instrument for multi-point malodorous gases, comprising an odor electronic nose instrument (I), a plurality of gas sampling heads (II), an external vacuum pump (III), an ambient air purification device (IV), a clean air cylinder (V), gas pipelines, an electronic hygrometer (VI), a central control room (VII) and a plurality of stationary/mobile terminals (VIII), for long-term cyclical monitoring of 10 malodorous pollution sites, and online estimation and prediction of multiple concentration control index values of malodorous gases;

wherein the odor electronic nose instrument (I) comprises a gas sensor array (I-1) and a thermostatic working room (I(a)) of the gas sensor array, a multi-point centralized auto-sampling system (I(b)), and a computer control and data analyzing system (1(c)); the thermostatic working room (I(a)) of the gas sensor array is comprised of the gas sensor array and an annular working chamber of the gas sensor array, a thermal insulation layer (I-2), a resistance heating wire (I-3) and a fan (I-4); the gas sensor array (I-1) is comprised of 16 gas sensors, which are uniformly distributed in a sealed chamber having a middle diameter of 140 mm and a section size of 21 mm×17 mm and forms the annular working chamber of the gas sensor array; the thermostatic working room (I(a)) is with a constant temperature of 55±0.1° C. and located at a top right of the odor electronic nose instrument (I);

wherein the multi-point centralized auto-sampling system (I(b)) comprises an internal miniature vacuum pump (I-14), a first two-position two-port electromagnetic valve (I-5), a second two-position two-port electromagnetic valve (I-6-1), a third two-position two-port electromagnetic valve (I-6-2), a fourth two-position two-port electromagnetic valve (I-6-3), a fifth two-position two-port electromagnetic valve (I-6-4), a sixth two-position two-port electromagnetic valve (I-6-5), a seventh two-position two-port electromagnetic valve (I-6-6), an eighth two-position two-port electromagnetic valve (I-6-7), a ninth two-position two-port electromagnetic valve (I-6-8), a tenth two-position two-port electromagnetic valve (I-6-9), an eleventh two-position two-port electromagnetic valve (I-6-10), a twelfth two-position two-port electromagnetic valve (I-8), a thirteenth two-position two-port electromagnetic valve (I-10), and a fourteenth two-position two-port electromagnetic valve (I-13), a throttle valve (I-11), a flowmeter (I-12), a vacuum pressure gauge (I-7), a gas buffer cavity (I-9), the multi-point centralized auto-sampling system (I(b)) is located at a lower right of the odor electronic nose instrument (I);

wherein the computer control and data analyzing system (I(c)) comprises a computer mainboard (I-15), a data acquisition card (I-16), a monitor (I-17), a drive and control circuit module (I-18), a precision linear and switching power module (I-19), a hard disk, a network card, a video card, the computer control and data analyzing system (I(c)) is located on a left side of the odor electronic nose instrument (I);

wherein the multi-point centralized auto-sampling system (I(b)) has a gas sampling period of $T_0$=180-300 s for a malodorous gas of a single monitoring point, with a default value $T_0$=240 s, so the gas sensor array (I-1) generates a 16-dimensional response vector for the single monitoring point;

according to the 16-dimensional response vector, using, by the computer control and data analyzing system (I(c)) is configured to use a cascade machine learning model to perform real-time analysis and prediction of an olfactory concentration value of the malodorous gas of the single monitoring point, concentrations of eight compounds specified in a Chinese National Standard GB14554-1993: $NH_3$, $H_2S$, $CS_2$, $C_3H_9N$, $CH_4S$, $C_2H_6S$, $C_2H_6S_2$, $C_8H_8$, and concentrations of $SO_2$ and the total volatile organic compound (TVOC) specified in a Chinese National Standard GB/T18883-2002, totaling 10+1 items; and finally transmit through wireless Internet, monitoring data and prediction results to the central control room (VII) and designated ones of the plurality of stationary/mobile terminals (VIII);

the odor electronic nose instrument (I) is configured to obtain the 16-dimensional response vector every single gas sampling period $T_0$, which is stored in a data file of a computer hard disk, use 10 two-position two-port electromagnetic valves from the second two-position two-port electromagnetic valve (I-6-1) to the eleventh two-position two-port electromagnetic valve (I-6-10) to sequentially control on-and-off of the malodorous gases at 10 monitoring points within a 4 km² area, online monitor the malodorous gases at the 10 monitoring points by using the cyclic sampling period of $T=10\times T_0$ to obtain 10 monitoring data results, and sequentially store the 10 monitoring data results in 10 data files, wherein the 10 monitoring data results are a numerical basis for the odor electronic nose instrument (I) to realize cyclically online quantitative prediction of 10+1 concentration control index values of the malodorous gases; wherein the gas sampling period $T_0$ comprises following five stages: an initial recovery stage of the gas sensor array lasting 95-215 s, an accurate calibration stage of clean air lasting 30 s, a balance stage lasting 5 s, a stage of a headspace sampling of the malodorous gases lasting 30 s and a flushing stage of purified ambient air lasting 20 s; in the gas sampling period $T_0$, under a control of a computer, a two-position two-port electromagnetic valve (I-6-$k$, $k$=1, 2, . . . , 10) corresponding to one of the 10 monitoring points is connected, and another nine two-position two-port electromagnetic valves corresponding to another nine of the 10 monitoring points are disconnected; the internal miniature vacuum pump (I-14) draws a malodorous gas into the gas buffer cavity (I-9) with a flow rate of 1,000 ml/min, thereby enabling the malodorous gas to flow through the annular working chamber of the gas sensor array and skim over surfaces of the sensitive films of the gas sensor array, so that the gas sensor array generates sensitive responses lasting 30 s; from a beginning of the balance stage, the computer control and data analyzing system (1(c)) continuously records sensitive response data, wherein the sensitive response data comprises response data of the gas sensor array in following three stages, which last 45 s: the balance stage lasting 5 s, the stage of the headspace sampling of the malodorous gases lasting 30 s, and the flushing stage of the purified ambient air lasting first 10 s, which are temporarily stored in a text file; response data of other time slots in the gas sampling period $T_0$ are not recorded; in the response data of 45 s, a difference between a steady-state maximum value and a minimum value of a response curve of a single gas sensor is extracted as a response component, so that the gas sensor array generates the 16-dimensional response vector; in 10 s after the end of the data recording, that is, a later 10 s of the purified ambient air flushing stage, the computer control and data analyzing system (I(c)) predicts the 10+1 concentration control index values of the malodorous gases based on the 16-dimensional response vector;

wherein the odor electronic nose instrument (I) is configured to perform long-term online monitoring of multiple monitoring points and online prediction of various concentration control index values of the malodorous gases in the pollution sites by executing the following operations:

(1), a power-on operation: when the odor electronic nose instrument (I) is preheated for 30 minutes and an "Air purifier on" option on a screen menu is clicked, triggering the ambient air purification device (IV) to start purifying an ambient air where the odor electronic nose instrument (I) is located, and keeping the ambient air purification device (IV) working until an "Air purifier off" option is clicked;

under a pumping action of the internal miniature vacuum pump (I-14) inside the ambient air purification device (IV), making the purified ambient air sequentially flow through the first two-position two-port electromagnetic valve (I-5), the annular working chamber of the gas sensor array (I-1) and the thirteenth two-position two-port electromagnetic valve (I-10) with a flow rate of 6,500 ml/min, and then be discharged to outdoor; wherein a temperature in the annular working chamber of the gas sensor array (I-1) reaches a constant 55±0.1° C. from a room temperature;

when an "External vacuum pump on" option on the screen menu is clicked; drawing, by the external vacuum pump (III) with a suction flow rate of 250-280 l/min and a limit vacuum degree of 100-120 mbar, a malodorous gas from a certain monitoring point to the odor electronic nose instrument (I) with a linear distance of up to 2.5 km to the odor electronic nose instrument (I) within 1 minute through a stainless steel pipe with an inner diameter of ϕ10 mm, and then making the malodorous gas from the certain monitoring point flow through a corresponding two-position two-port electromagnetic valve (I-6-$k$) k=1, 2, . . . , 10, the vacuum pressure gauge (I-7) and the gas buffer cavity (I-9) and be directly discharged to outdoor; keeping, by the external vacuum pump (III) pump the malodorous gas from the certain monitoring point until an "external vacuum pump off" option on the screen menu is clicked;

modifying a setting of the gas sampling period $T_0$ on the screen menu as a default value $T_0$=40 minutes and modifying a cycle sampling period of malodorous gases for 10 monitoring points as T=10×$T_0$;

(2), an operation for starting a cyclic sampling period of the malodorous gases: when a "start detection" button on the screen menu is clicked, sequentially monitoring, by the odor electronic nose instrument (I), the 10 monitoring points, and automatically generating, by the computer control and data analyzing system (I(c)), 10 text files in a designated folder to store the response data of the gas sensor array (I-1) to the malodorous gases at 10 monitoring points;

(3), an operation for starting a single sampling period of the malodorous gas for a monitoring point k; taking $T_0$=240 seconds as an example, wherein k=1, 2, . . . , 10:

(3.1), a preliminary recovery operation of the gas sensor array (I-1): in the 0-155 s of the gas sampling period $T_0$, under the pumping action of the internal miniature vacuum pump (I-14) inside the ambient air purification device (IV), making the purified ambient air sequentially flow through the first two-position two-port electromagnetic valve (I-5), the annular working chamber of the gas sensor array (I-1), the thirteenth two-position two-port electromagnetic valve (I-10) with a flow rate of 6,500 ml/min, and then be discharged to the outdoor; so that the accumulated heat in the annular working chamber of the gas sensor array (I-1) is taken away under an action of the 6,500 ml/min purified ambient air, the malodorous gas molecules adhered to the sensitive membrane surfaces of the gas sensor array (I-1) and the inner wall of pipelines are preliminarily washed away, and the gas sensor array (I-1) preliminarily returns to a reference state which lasts 155 s; wherein among 10 two-position two-port electromagnetic valves from the first second two-position two-port electromagnetic valve (I-6-1) to the eleventh two-position two-port electromagnetic valve (I-6-10), only one two-position two-port electromagnetic valve (I-6-$k$) is on, another nine two-position two-port electromagnetic values are off, and the external vacuum pump (III) pumps the malodorous gas in the monitoring point k into the odor electronic nose instrument (I), wherein k=1, 2, . . . , 10;

(3.2), an accurate calibration operation of the gas sensor array by clean air: in 156-185 s range of the gas sampling period $T_0$, when the fourteenth two-position two-port electromagnetic valve (I-13) is on, the first two-position two-port electromagnetic valve (I-5), the twelfth two-position two-port electromagnetic valve (I-8), and the thirteenth two-position two-port electromagnetic valve (I-10) are off, and among the 10 two-position two-port electromagnetic valves from the first second two-position two-port electromagnetic valve (I-6-1) to the eleventh two-position two-port electromagnetic valve (I-6-10), only the one two-position two-port electromagnetic valve (I-6-$k$) is on, the other nine two-position two-port electromagnetic values are off; under the pumping action of the internal miniature vacuum pump (I-14) inside the ambient air purification device (IV), making the clean air sequentially flow through the fourteenth two-position two-port electromagnetic valve (I-13), the gas pipelines, the annular working chamber of the gas sensor array (I-1), the throttle valve (I-11), the flowmeter (I-12) and the internal miniature vacuum pump (I-14) with the flow rate of 1,000 ml/min, and then be discharged to the outdoor; wherein the clean air makes the gas sensor array (I-1) accurately return to the reference state which lasts 30s; and the external vacuum pump (III) keeps pumping for 30 seconds;

(3.3), an operation of a balance stage: in 186-190 s of the gas sampling period $T_0$, when the first two-position two-port electromagnetic valve (I-5), the twelfth two-position two-port electromagnetic valve (I-8), the thirteenth two-position two-port electromagnetic valve (I-10) and the fourteenth two-position two-port electromagnetic valve (I-13) are disconnected, among the 10 two-position two-port electromagnetic valves from the first second two-position two-port electromagnetic valve (I-6-1) to the eleventh two-position two-port electromagnetic valve (I-6-10), only the one two-position two-port electromagnetic valve (I-6-$k$) is on, the other nine two-position two-port electromagnetic values are off; and there is no gas flow in the annular working chamber of the gas sensor array (I-1); from $186^{th}$ second of the gas sampling period $T_0$, recording and storing, by the computer control and data analyzing system (I(c)), real-time response data of the gas sensor array (I-1) in a designated temporary text file "temp.txt"; wherein the external vacuum pump (III) keeps drawing the malodorous gas for 5 seconds;

(3.4), the headspace sampling operation of the malodorous gas at the monitoring point k: in 190-220 seconds of the gas sampling period $T_0$, when the twelfth two-position two-port electromagnetic valve (I-8) is on, the first two-position two-port electromagnetic valve (I-5), the fourteenth two-position two-port electromagnetic valve (I-13) and the thirteenth two-position two-port electromagnetic valve (I-10) are off, and among the 10 two-position two-port electromagnetic valves from the first second two-position two-port electromagnetic valve (I-6-1) to the eleventh two-position two-port electromagnetic valve (I-6-10), only the one two-position two-port electromagnetic valve (I-6-k) is on, the other nine two-position two-port electromagnetic values are off; under the pumping action of the internal miniature vacuum pump (I-14) inside the ambient air purification device (IV), making the malodorous gas in the gas buffer cavity (I-9) sequentially flow through the annular working chamber of the gas sensor array (I-1), the throttle valve (I-11), the flowmeter (I-12), the internal miniature vacuum pump (I-14) with a flow rate of 1,000 ml/min, and be finally discharged to the outdoor; wherein sensitive responses of the gas sensor array (I-1) are recorded in the temporary file "temp.txt", and the external vacuum pump (III) keeps pumping for 30 seconds;

(3.5), a flushing operation of the gas sensor array: in the 221-230 seconds of the gas sampling period $T_0$, when the first two-position two-port electromagnetic valve (I-5) and the thirteenth two-position two-port electromagnetic valve (I-10) are connected, and the twelfth two-position two-port electromagnetic valve (I-8) and the fourteenth two-position two-port electromagnetic valve (I-13) are disconnected; under the pumping action of the internal miniature vacuum pump (I-14) inside the ambient air purification device (IV), making the purified ambient air sequentially flows through the first two position two-port solenoid valve (I-5), the annular working chamber of the gas sensor array (I-1) and the thirteenth two-position two-port electromagnetic valve (I-10) with a flow rate of 6,500 ml/min, and then be discharged to the outdoor;

at the same time, among the 10 two-position two-port electromagnetic valves from the first second two-position two-port electromagnetic valve (I-6-1) to the eleventh two-position two-port electromagnetic valve (I-6-10), only one two-position two-port electromagnetic valve (I-6-(k+1)) is on, another nine two-position two-port electromagnetic valves are off, and pumping, by the external vacuum pump (III), the malodorous gas at a monitoring point (k+1); due to the role of the purified ambient air, the accumulated heat in the annular working chamber of the gas sensor array (I-1) is taken away, the malodorous gas molecules adhered to the sensitive film surfaces of the gas sensor array (I-1) and the inner walls of the pipelines are preliminarily washed away, and the gas sensor array (I-1) gradually returns to the reference state, which takes 20 seconds, wherein:

(a), in the 221-230 seconds of the gas sampling period $T_0$, continuing to record the response data of the gas sensor array in the temporary file "temp.txt" which lasts 10 s; at the end of $230^{th}$ second, stopping, by the computer control and data analyzing system (I(c)), recording the response data of the gas sensor array;

(b), in the 231-240 seconds of the gas sampling period $T_0$, performing, by the computer control and data analyzing system (I(c)), following three operations:

(b1), a feature extraction: from the $231^{st}$ second, extracting the maximum and the minimum steady-state response values of each gas sensor with a time duration of 45 seconds from the temporary file "temp.txt", and taking and recording a difference between the maximum and the minimum response value as a characteristic response component $x_i(t)$ of each gas sensor to the malodorous gas at the monitoring point k at the current time t in a corresponding data file, wherein i=1, 2, . . . , 16;

(b2), a response prediction of the gas sensor array: realizing, by the first level of the cascade machine learning model, an online self-learning according to the time-series response vectors of the gas sensor array within a period that have occurred before the current time t, and predicting responses of the gas sensor array (I-1) at a future time points of $T_0$, $2T_0$ and $3T_0$; wherein the first level of the cascade machine learning model is 16*3 convolutional neural networks and the period comprises three time segments of [t−18, t], [t−19, t−1] and [t−20, t−2];

(b3), a prediction of malodorous gas concentration control index values: continuing to predict, by the second level of the cascade machine learning model, the 10+1 concentration control index values of the malodorous gas at the monitoring point k according to the response values of the gas sensor array predicted by the 16*3 convolution neural networks in the first level of the cascade model, showing the 10+1 concentration control index values on the monitor, and transmitting monitoring and prediction results to a central control room (VII) and the plurality of stationary/mobile terminals (VIII) through the Internet network wherein the second level of the cascade machine learning model is 10+1 deep neural networks;

(3.6), an ending operation of the gas sampling period $T_0$ at the monitoring point k: k←k+1, returning to the step (3.1), and starting the gas sampling period $T_0$ at the monitoring point (k+1); if k+1>10, then starting to detect a malodorous gas at a monitoring point k=1 of a next gas sampling period;

repeating the steps (3.1)~(3.6); so that the odor electronic nose instrument (I) realizes cyclically online measurement, identification and prediction of 10+1 concentration control index values of malodorous gases at 10 monitoring points.

2. The system according to claim 1, wherein the gas sensor array (I-1) is comprised of 11 metal oxide semiconducting (MOS) elements, 4 electrochemical (EC) elements and a photo ionization detector (PID); wherein the 11 MOS elements are configured to detect a plurality of organic/inorganic compounds; the 4 EC elements are configured to detect 4 inorganic compounds: $NH_3$, $H_2S$, $CS_2$ and $SO_2$; the PID is configured to detect a total volatile organic compound (TVOC).

3. The system according to claim 1, wherein the online multi-point centralized monitoring and analysis system is operative to realize online monitoring and analysis of multi-point malodorous gases in a certain specific area; and 10 monitoring points are set in a maximum area of 2 km*2 km=4 $km^2$, including 9 stationary monitoring points and 1 mobile monitoring point; the odor electronic nose instrument (I) is located indoor, which connects with each of the 10 monitoring points through a stainless steel pipe with an inner diameter of ϕ10 mm; each gas sampling head is in a form of a water tap, is connected to a commercial dedusting, dehumidification and purification part, and is installed or moved to a designated position; when a monitoring point is changed, the stainless steel pipe is relayed and the gas sampling head is re-installed and re-moved to the designated position.

4. The system according to claim 1, wherein
eight or more of the 10 monitoring points are arranged around a boundary of a specified area, and a target is to make stainless steel pipelines between the odor electronic nose instrument (I) and the 10 monitoring points be a shortest value;

for an area with accessible paths, the odor electronic nose instrument (I) is configured to be arranged indoor in a center of the area, wherein the area with accessible paths comprises a chemical industrial park, and a residential area;

for an area without accessible paths, the odor electronic nose instrument (I) is configured to be arranged indoor at a boundary of the area, wherein the area without accessible paths comprises a landfill, and a sewage treatment plant.

5. The system according to claim 1, wherein the external vacuum pump (III) has a suction rate of 250-280 l/min, a limit vacuum degree of 100-120 mbar, and is operative to work continuously for a long period of time;

the external vacuum pump (III) is configured to draw a malodorous gas at one of the 10 monitoring points with a linear distance of 2.5 km into the odor electronic nose instrument (I) through a stainless steel pipe of a $\phi 10$ mm inner diameter within less than 1 min; and in the gas sampling period $T_0$, except for a 30 s headspace sampling stage, the external vacuum pump (III) is configured to make the malodorous gas flow into the odor electronic nose instrument (I) and be discharged to the outdoor directly, but not flow through the annular working chamber of the gas sensor array (I-1).

6. The system according to claim 1, wherein the gas buffer cavity (I-9) has a size of $\phi 40$ min*5 mm and is set inside the odor electronic nose instrument (I); a flow rate of the malodorous gas measured in the gas buffer cavity (I-9) is 16 times lower than a flow rate in the stainless steel pipe with an inner diameter of $\phi 10$ mm; only at a 30 s headspace sampling stage, the internal miniature vacuum pump (I-14) is configured to draw the malodorous gas in the gas buffer cavity (I-9) into the annular working chamber of the gas sensor array (I-1), such that the gas sensor array (I-1) generates a sensitive response; wherein the malodorous gas pumped by the internal miniature vacuum pump (I-14) are fresh malodorous gases.

7. The system according to claim 1, wherein
before a headspace sampling stage of the malodorous gas, an accurate calibration stage of clean air, lasting 30 s and having 1,000 ml/min, makes multiple perceptions of the malodorous gas by the gas sensor array (I-1) on a same baseline; a standard volume of a 12-15 MPa clean air cylinder (V) is 40 L, and is 6 m³ when the standard volume is converted to normal temperature and pressure;

when the gas sampling period $T_0$=3, 4 and 5 minutes, a bottle of 40 L compressed clean air is respectively used for 25, 33 and 41 days; and an outdoor ambient air where the odor electronic nose instrument (I) is located is first purified by the ambient air purification device (IV), and then is used to flush the gas sensor array (I-1), so as to primarily restore the gas sensor array (I-1) to a reference state and reduce an operation cost.

8. The system according to claim 1, wherein a set of big data of the malodorous gases comprises:
(1), online detection data monitored by the gas sensor array (I-1) for a large number of malodorous pollutants on chemical industrial parks including fragrance and flavor factories, pharmaceutical factories, landfill sites, sewage treatment plants, and farms;

(2), off-line laboratory test data monitored by the gas sensor array (I-1) for a large number of headspace volatile gases of standard malodorous samples, including 5 standard odorants specified in a Chinese National Standard GB/T14675-1993, the standard malodorous samples made up of nine single-component malodorous pollutants with different concentrations designated by GB14554-1993: $C_3H_9N$, $C_8H_8$, $H_2S$, $CH_4S$, $C_2H_6S$, $C_2H_6S_2$, $NH_3$, $CS_2$, and $SO_2$ by GB/T18883-2002, and standard malodorous samples of mixed components prepared with different concentrations of multiple single compounds, wherein the 5 standard odorants comprise β-phenylethanol, isovaleric acid, methylcyclopentanone, peach aldehyde and β-methylindole;

(3), off-line panel evaluation data of dimensionless concentration OU values specified in GB/T14675-1993 and a Chinese Industry Standard HJ905-2017 for the malodorous gases sampled by vacuum bottles or bags at a large number of malodorous sites and immediately transported back to olfactory rooms;

(4), off-line TVOC data by gas chromatography, and off-line $SO_2$ data obtained by spectrophotometry, depending upon the malodorous pollutants in GC adsorption tubes sampled on sites according to GB/T18883-2002;

(5), off-line laboratory test data of 8 malodorous components specified in Chinese National Standards from GB/T14676-1993 to GB/T14680-1993 by gas chromatography, mass spectrometry and spectrophotometry for the on-site sampling malodorous pollutants; and (6), residents' complaint data in vicinities of malodorous pollution sources.

9. The system according to claim 1, wherein the odor electronic nose instrument (I) is configured to use the cascade machine learning model to predict olfactory concentration values of the malodorous gases and several specified concentration control index values of malodorous pollutants at time points of t+1, t+2 and t+3 in a near future;

wherein a first level of the cascade machine learning model, is responsible for predicting responses of the gas sensor array (I-1) to the malodorous gases at the time points of t+1, t+2 and t+3, based on occurred time-series responses of the gas sensor array (I-1) at a current time t and a recent past, wherein the first level of the cascade machine learning model is a convolutional neural network layer;

wherein a second level of the cascade machine learning model, further predicts the olfactory concentration values of the malodorous gases and multiple specified concentration control index values of various malodorous pollutants at the time points of t+1, t+2 and t+3, based on long-term accumulation of malodorous gas big data and prediction values of the first-level, wherein the second level of the cascade machine learning model is the deep neural network layer.

10. The system according to claim 1, wherein
according to a "divide-and-conquer" strategy, a first level of the cascade machine learning model is configured to use 16*3 groups of single-output single-hidden-layer convolution neural networks to predict responses of each gas sensor at time points of t+1, t+2 and t+3; for a single period of $T_0$=4 minutes, predict responses at 40, 80 and 120 minutes in a coming future from a current time t;

when three single-output single-hidden-layer convolution neural network modules with the gas sampling period $T_0=4$ minutes are used to respectively predict the responses of a gas sensor i at time points of t+1, t+2 and t+3:

(a), a single-output single-hidden-layer convolution neural network $CNN_{i1}$ is configured to predict a response of a gas sensor i at the time point of t+1:

if the convolutional neural network $CNN_{i1}$ is used to learn 18 time-series response data of the gas sensor i that have occurred before the current time t, a delay length $\Delta t=9$, then a number of input nodes is $m_i=9$, a number of hidden nodes is $h_i=5$, and a number of output nodes is $n_i=1$; a preprocessed time-series response data set $X_{i1}$ of the gas sensor i learned online by the convolutional neural network $CNN_{i1}$ is:

$$X_{i1} = \begin{pmatrix} x_i(t-9) & x_i(t-8) & x_i(t-7) & x_i(t-6) & x_i(t-5) \\ x_i(t-4) & x_i(t-3) & x_i(t-2) & x_i(t-1) & \\ x_i(t-10) & x_i(t-9) & x_i(t-8) & x_i(t-7) & x_i(t-6) \\ x_i(t-5) & x_i(t-4) & x_i(t-3) & x_i(t-2) & \\ & & \cdots & & \\ x_i(t-17) & x_i(t-16) & x_i(t-15) & x_i(t-14) & x_i(t-13) \\ x_i(t-12) & x_i(t-11) & x_i(t-10) & x_i(t-9) & \\ x_i(t-18) & x_i(t-17) & x_i(t-16) & x_i(t-15) & x_i(t-14) \\ x_i(t-13) & x_i(t-12) & x_i(t-11) & x_i(t-10) & \end{pmatrix} \in R^{10 \times 9}$$

the target output is:

$d_{i1}=(x_i(t)x_i(t-1)x_i(t-2)x_i(t-3)x_i(t-4)x_i(t-5)x_i(t-6)x_i(t-7)x_i(t-8)x_i(t-9))^T \in R^{10}$;

the convolutional neural network $CNN_{i1}$ is configured to learn a 18-dimensional time-series responses of the gas sensor i that have occurred in last 12 hours, generate ten 9-dimensional time-series response samples, wherein the ten 9-dimensional time-series response samples represent that a number of samples is $N_{i1}=10$;

when activation functions of hidden and output layers in the $CNN_{i1}$ are a modified Sigmoid function $f(\varphi)=3/(1+\exp(-\varphi/3))$, and an error back propagation algorithm is adopted, wherein a learning factor is $\eta_i=5/N_{i1}=0.2$; the data set $X_{i1}$ and the target output $d_{i1}$ are transformed to a range of [0, 3];

by undergoing an online learning in 10 seconds, the convolutional neural network $CNN_{i1}$ is configured to predict a response $x_i(t+1)$ of the gas sensor i at the time point of t+1, according to a following 9-d time-series response in a latest time period:

$x_{i1}=(x_i(t-8)x_i(t-7)x_i(t-6)x_i(t-5)x_i(t-4)x_i(t-3)x_i(t-2)x_i(t-1)x_i(t))^T \in R^9$ when $T_0=4$ minutes, the convolutional neural network CNNi1 is configured to predict a response of the gas sensor i in a next 40 minutes;

(b), two single-output single-hidden-layer convolution neural networks $CNN_{i2}$ and $CNN_{i3}$ are configured to predict responses of the gas sensor i at the time points of t+2 and t+3:

structures of the convolutional neural networks $CNN_{i2}$ and $CNN_{i3}$ are $m_i=9$, $h_i=5$, and $n_i=1$; and pre-processed data sets $X_{i2}$ and $X_{i3}$ online learned are respectively:

$$X_{i2} = \begin{pmatrix} x_i(t-10) & x_i(t-9) & x_i(t-8) & x_i(t-7) & x_i(t-6) \\ x_i(t-5) & x_i(t-4) & x_i(t-3) & x_i(t-2) & \\ x_i(t-11) & x_i(t-10) & x_i(t-9) & x_i(t-8) & x_i(t-7) \\ x_i(t-6) & x_i(t-5) & x_i(t-4) & x_i(t-3) & \\ & & \cdots & & \\ x_i(t-18) & x_i(t-17) & x_i(t-16) & x_i(t-15) & x_i(t-14) \\ x_i(t-13) & x_i(t-12) & x_i(t-11) & x_i(t-10) & \\ x_i(t-19) & x_i(t-18) & x_i(t-17) & x_i(t-16) & x_i(t-15) \\ x_i(t-14) & x_i(t-13) & x_i(t-12) & x_i(t-11) & \end{pmatrix} \in R^{10 \times 9}$$

and $$X_{i3} = \begin{pmatrix} x_i(t-11) & x_i(t-10) & x_i(t-9) & x_i(t-8) & x_i(t-7) \\ x_i(t-6) & x_i(t-5) & x_i(t-4) & x_i(t-3) & \\ x_i(t-12) & x_i(t-11) & x_i(t-10) & x_i(t-9) & x_i(t-8) \\ x_i(t-7) & x_i(t-6) & x_i(t-5) & x_i(t-4) & \\ & & \cdots & & \\ x_i(t-19) & x_i(t-18) & x_i(t-17) & x_i(t-16) & x_i(t-15) \\ x_i(t-14) & x_i(t-13) & x_i(t-12) & x_i(t-11) & \\ x_i(t-20) & x_i(t-19) & x_i(t-18) & x_i(t-17) & x_i(t-16) \\ x_i(t-15) & x_i(t-14) & x_i(t-13) & x_i(t-12) & \end{pmatrix} \in R^{10 \times 9}$$

wherein $X_{i2}$ and $X_{i3}$ each have the ten 9-dimensional time-series response sample, and have a same number of samples $N_{i2}=N_{i3}=N_{i1}=10$; target outputs and depended time-series responses of $CNN_{i2}$ and $CNN_{i3}$ are similarly to the target output and the time-series of the $CNN_{i1}$; when $T_0=4$ minutes, the two single-output single-hidden-layer convolution neural networks CNNi2 and CNNi3 are configured to learn responses of the gas sensor i in 12 hours before 40 and 80 minutes, respectively predicting the responses $x_i(t+2)$ and $x_i(t+3)$ of the gas sensor i in the time points of t+2 and t+3, wherein predicting the responses $x_i(t+2)$ and $x_i(t+3)$ of the gas sensor i in the time points of t+2 and t+3 represents that predicting responses of the gas sensor i in next 80 and 120 minutes.

11. The system according to claim 1, wherein according to a "divide-and-conquer" strategy, an overall prediction problem of 10+1 concentration control index values of malodorous gases, including $NH_3$, $H_2S$, $CS_2$, $C_3H_9N$, $CH_4S$, $C_2H_6S$, $C_2H_6S_2$, $C_8H_8$, $SO_2$, TVOC and the olfactory concentration values of the malodorous gases is divided into 11 single concentration prediction problems;

in a second level of the cascade machine learning model is configured to use 10+1 single-output three-hidden-layer deep neural network modules to predict a 10+1 malodorous pollution control index values; wherein a training set of a single-output deep neural network is big data online detected by the gas sensor array (I-1) of the odor electronic nose instrument (I) for standard malodorous liquid/gas samples and a large number of malodorous pollutants; wherein target outputs are the malodorous olfactory values, off-line measurement values of conventional instruments such as a gas chromatographer, mass spectrometer and spectrophotometer, and data of residents' complaints;

each single-output three-hidden-layer deep neural network $DNN_j$ is configured to adopt a bottom-up off-line learning manner; wherein parameters of a first hidden layer and a second hidden layer are determined by a single-hidden-layer peer-to-peer neural network, wherein the single-hidden-layer peer-to-peer neural network represents that weights of a hidden-to-output layer are directly equal to weights of an input-to-hidden layer and target outputs are directly equal to input values of the peer-to-peer network; wherein input and output components are proportionally transformed to a range of [0, 3]; wherein an activation function of hidden units of each single-hidden-layer peer-to-peer neural network are modified sigmoid functions $f(\varphi)=3/(1+\exp(-\varphi/3))$, an error back-propagation algorithm is adopted, a learning factor is $\eta_j=1/N_j$, and the hidden-to-output layer is discarded after ending a learning operation, wherein $N_j$ is a number of samples in the odor big data;

a $j^{th}$ single-output deep neural network $DNN_j$ is configured to, based on the predicted responses of 16 convolutional neural networks to the gas sensor array (I-1) at the time point of t+1, $\{x_1(t+1), x_2(t+1), \ldots, x_{16}(t+1)\}$, predict a $j^{th}$ concentration index value $y_i(t+1)$ of the malodorous gas at the time point of t+1;

the $DNN_j$ is configured to, according to the predicted responses of 16 convolutional neural networks, $\{x_1(t+2), x_2(t+2), \ldots, x_{16}(t+2)\}$ and $\{x_1(t+3), x_2(t+3), \ldots, x_{16}(t+3)\}$, respectively predict $j^{th}$ concentration index values $y_i(t+2)$ and $y_i(t+3)$ of the malodorous gas at the time points of t+2 and t+3;

if an actual input is a current response vector of the gas sensor array, $x(t)=(x_1(t), x_2(t), \ldots, x_{16}(t))^T$, a temperature and humidity values at the time t are added if necessary, wherein an actual output of $DNN_j$ is an estimation of a current concentration value $y_i(t)$ of a component j of the malodorous gas.

* * * * *